US008901350B2

(12) United States Patent
Schneider et al.

(10) Patent No.: US 8,901,350 B2
(45) **Date of Patent: *Dec. 2, 2014**

(54) PROCESS FOR THE PREPARATION OF FORMIC ACID

(75) Inventors: Daniel Schneider, Mannheim (DE); Klaus-Dieter Mohl, Hockenheim (DE); Martin Schäfer, Grünstadt (DE); Karin Pickenäcker, Lampertheim (DE); Stefan Rittinger, Mannheim (DE); Thomas Schaub, Neustadt (DE); Joaquim Henrique Teles, Otterstadt (DE); Rocco Paciello, Bad Dürkheim (DE); Gerd Kaibel, Lampertheim (DE)

(73) Assignee: BASF SE (DE)

( * ) Notice: Subject to any disclaimer, the term of this patent is extended or adjusted under 35 U.S.C. 154(b) by 705 days.

This patent is subject to a terminal disclaimer.

(21) Appl. No.: 13/171,598

(22) Filed: Jun. 29, 2011

(65) Prior Publication Data

US 2011/0319657 A1 Dec. 29, 2011

Related U.S. Application Data

(60) Provisional application No. 61/359,382, filed on Jun. 29, 2010, provisional application No. 61/392,062, filed on Oct. 12, 2010.

(51) Int. Cl.
*C07C 51/44* (2006.01)
*C07C 51/09* (2006.01)

(52) U.S. Cl.
CPC ................ *C07C 51/09* (2013.01); *C07C 51/44* (2013.01)
USPC .......................................... 562/609; 562/608

(58) Field of Classification Search
CPC ............................... C07C 51/44; C07C 51/09
USPC ................................................. 562/608, 609
See application file for complete search history.

(56) References Cited

U.S. PATENT DOCUMENTS

| | | | | |
|---|---|---|---|---|
| 4,218,568 | A | 8/1980 | Hohenschutz et al. | |
| 5,294,740 | A | 3/1994 | Kiefer et al. | |
| 8,426,641 | B2 * | 4/2013 | Schaub et al. | 562/609 |
| 2008/0097126 | A1 | 4/2008 | Karl et al. | |
| 2010/0063320 | A1 | 3/2010 | Challand et al. | |
| 2010/0126843 | A1 | 5/2010 | Stabel et al. | |

FOREIGN PATENT DOCUMENTS

| | | | |
|---|---|---|---|
| DE | 2545658 | A1 | 4/1977 |
| DE | 3428319 | A1 | 2/1986 |
| DE | 102009046310 | A1 | 5/2010 |
| EP | 0 001 432 | A1 | 4/1979 |
| EP | 0126524 | A1 | 11/1984 |
| EP | 0181078 | A1 | 5/1986 |
| EP | 0563831 | A2 | 10/1993 |
| GB | 1554172 | A | 10/1979 |
| WO | WO-2006/021411 | A1 | 3/2006 |
| WO | WO-2008/116799 | A1 | 10/2008 |
| WO | WO-2010/149507 | A2 | 12/2010 |

OTHER PUBLICATIONS

U.S. Appl. No. 61/316,841.
U.S. Appl. No. 61/359,405.

* cited by examiner

*Primary Examiner* — Yevegeny Valenrod
(74) *Attorney, Agent, or Firm* — Drinker Biddle & Reath LLP

(57) ABSTRACT

Process for obtaining formic acid by thermal separation of a stream comprising formic acid and a tertiary amine (I), in which a liquid stream comprising formic acid and a tertiary amine (I) in a molar ratio of from 0.5 to 5 is produced by combining tertiary amine (I) and a formic acid source, from 10 to 100% by weight of the secondary components present therein are separated off and formic acid is removed by distillation in a distillation apparatus at a bottom temperature of from 100 to 300° C. and a pressure of from 30 to 3000 hPa abs from the liquid stream obtained, the bottom discharge from the distillation apparatus being separated into two liquid phases and the upper liquid phase being recycled to the formic acid source and the lower liquid phase being recycled for separating off the secondary components and/or to the distillation apparatus.

11 Claims, 15 Drawing Sheets

PROCESS FOR THE PREPARATION OF FORMIC ACID

RELATED APPLICATIONS

The present application incorporates the provisional U.S. applications No. 61/392,062 and No. 61/359,382, filed on Oct. 12, 2010, and Jun. 29, 2010, by reference.

BACKGROUND OF THE INVENTION

The present invention relates to a process for obtaining formic acid by thermal separation of a stream comprising formic acid and a tertiary amine (I), in which a liquid stream comprising formic acid and a tertiary amine (I) in a molar ratio of from 0.5 to 5 is produced by combining tertiary amine (I) and a formic acid source, from 10 to 100% by weight of the secondary components present therein are separated off, and formic acid is removed by distillation in a distillation apparatus at a bottom temperature of from 100 to 300° C. and a pressure of from 30 to 3000 hPa abs from the liquid stream obtained.

Formic acid is an important and widely useable product. It is used, for example, for acidification in the production of feeds, as preservative, as a disinfectant, as an assistant in the textile and leather industry, as a mixture with salts for deicing aircraft and runways and as a synthon in the chemical industry.

Perhaps the commonest process at present for the preparation of formic acid is the hydrolysis of methyl formate, which can be obtained, for example, from methanol and carbon monoxide. The aqueous formic acid obtained by hydrolysis is subsequently concentrated, for example by use of an extracting agent such as, for example, a dialkylformamide (DE 25 45 658 A1).

In addition, it is known that formic acid can also be obtained by thermal cleavage of compounds of formic acid and a tertiary nitrogen base. These compounds are in general acid ammonium formates of tertiary nitrogen bases, in which the formic acid has reacted beyond the stage of classic salt formation with the tertiary nitrogen bases to give stable addition compounds bridged via hydrogen bridge bonds. The addition compounds of formic acid and tertiary nitrogen bases can be formed by combining the tertiary nitrogen base and a formic acid source. Thus, for example, WO 2006/021,411 discloses the preparation of such addition compounds in general (i) by direct reaction of the tertiary nitrogen base with formic acid, (ii) by transition metal-catalyzed hydrogenation of carbon dioxide to give formic acid in the presence of the tertiary nitrogen base, (iii) by reaction of methyl formate with water and subsequent extraction of the resulting formic acid with the tertiary nitrogen base, and (iv) by reaction of methyl formate with water in the presence of the tertiary nitrogen base.

The general advantages of the use of addition compounds of formic acid and tertiary nitrogen bases for obtaining formic acid are that firstly the addition compounds initially bind formic acid sufficiently strongly to remove the formic acid as free formic acid from the medium, for example the reaction medium, in which the formic acid is first formed by chemical synthesis or, for example, from a dilute formic acid solution and to enable the formic acid to be separated off more easily thereby in the form of its addition compounds, and secondly the addition compounds are sufficiently weak to release the formic acid again subsequently by thermal cleavage in order to concentrate it and to obtain it purified in free form.

EP 0 001 432 A discloses a process for obtaining formic acid by hydrolysis of methyl formate in the presence of a tertiary amine, in particular of an alkylimidazole, with formation of addition compounds of formic acid and the tertiary amine. The hydrolysis mixture obtained, which comprises unreacted methyl formate, water, methanol, addition compounds and tertiary amine, is freed from the low boilers methyl formate and methanol in a first distillation column. In a second column, the remaining bottom product is dewatered. The dewatered bottom product of the second column, which still comprises addition compounds and tertiary amine, is then fed to a third column and the addition compounds are thermally cleaved therein into formic acid and tertiary amine. The formic acid liberated is removed as top product. The tertiary amine collects in the bottom and is recycled to the hydrolysis.

DE 34 28 319 A discloses a process for obtaining formic acid by hydrolysis from methyl formate. The hydrolysis mixture obtained, which comprises unreacted methyl formate, water, methanol and formic acid, is freed from the low boilers methyl formate and methanol in a first distillation column. The aqueous formic acid occurring in the bottom is then extracted with a higher-boiling amine, in particular a longer-chain, hydrophobic $C_6$- to $C_{14}$-trialkylamine, in the presence of an additional hydrophobic solvent, in particular of an aliphatic, cycloaliphatic or aromatic hydrocarbon, and converted thereby into an aqueous addition compound of formic acid and the amine. This is dewatered in a second distillation column. The dewatered addition compound occurring in the bottom is then fed to the uppermost tray of the distillation column (designated as "K4" in FIG. 1) and thermally cleaved according to DE 34 28 319 A. The hydrophobic solvent is present both in the top and in the bottom of the column. The gaseous top stream comprises in particular the liberated formic acid in addition to the hydrophobic solvent. This stream is liquefied again in a condenser. Two phases form, namely a polar formic acid phase and a hydrophobic solvent phase. The formic acid phase is taken off as product, and the solvent phase is recycled to the column as reflux. Owing to the presence of the hydrophobic solvent, it is possible to achieve complete cleavage of the adduct which, according to the teaching of the DE-A, allegedly takes place without decomposition of formic acid. The (almost) formic acid-free bottom product comprises the hydrophobic amine and the hydrophobic solvent. Said bottom product is recycled to the extraction stage.

EP 0 181 078 A and EP 0 126 524 A describe processes for obtaining formic acid by hydrogenation of carbon dioxide in the presence of a transition metal catalyst and of a tertiary amine, such as, for example, a $C_1$- to $C_{10}$-trialkylamine, with the formation of an addition compound of formic acid and the tertiary amine, working-up of the hydrogenation discharge with separation of the catalyst and the low boilers, exchange of the adduct base for a weaker, higher-boiling tertiary amine, in particular for an alkylimidazole, with separation of the first tertiary amine and subsequent thermal cleavage of the newly formed addition compound in a distillation column. For this purpose, according to EP 0 181 078 A, FIG. 1, the stream comprising formic acid and amine is fed into the middle region of the column "30". The formic acid liberated in the thermal cleavage is removed as top product. The weaker, higher-boiling tertiary amine collects in the bottom and is recycled to the base exchange stage.

WO 2008/116,799 discloses a process for obtaining formic acid by hydrogenation of carbon dioxide in the presence of a transition metal catalyst, a high-boiling polar solvent, such as, for example, an alcohol, ether, sulfolane, dimethyl sulfoxide or amide, and a polar amine carrying at least one hydroxyl group, to form an addition compound of formic acid and the amine. According to the teaching of WO 2008/116,799, the hydrogenation discharge can be fed directly to a distillation apparatus for the thermal cleavage of the addition compound. Said distillation apparatus may comprise a distillation column and, if short residence times are desired, also a thin-film or falling-film evaporator. The formic acid liberated is removed as top product. The polar amine and the polar solvent and any catalyst not separated off collect in the bottom and can be recycled to the hydrogenation stage.

WO 2006/021,411 describes a process for obtaining formic acid by thermal cleavage of an addition compound of formic acid and a tertiary amine (quaternary ammonium formate), in which the tertiary amine has a boiling point of from 105 to 175° C. Alkylpyridines are mentioned as preferred tertiary amines. The color stability of the formic acid obtained is increased by the special boiling range of the tertiary amines. The addition compound to be used can generally be obtained from the tertiary amine and a formic acid source. Advantageously, the discharge from the adduct synthesis is first freed from volatile constituents and then fed to the thermal cleavage. The thermal cleavage takes place as usual in a distillation column, the stream comprising formic acid and amine being fed according to FIG. 1 into the middle range of the column (C). The formic acid liberated is removed as top product. The tertiary amine, which may optionally still comprise residues of formic acid, collects in the bottom and can be recycled to the formic acid source.

EP 0 563 831 A mentions an improved process for the thermal cleavage of an addition compound of formic acid and a tertiary amine (quaternary ammonium formate) to obtain formic acid. The addition compound to be used can generally be obtained from the tertiary amine and a formic acid source. Advantageously, the discharge from the synthesis is first freed from volatile constituents and then fed to the thermal cleavage in the middle of a distillation column. The improvement substantially consists in carrying out the thermal cleavage of the addition compound in the presence of a secondary formamide which increases the color stability of the formic acid obtained. The formic acid liberated is removed as top product. The tertiary amine and the secondary formamide collect in the bottom and can be recycled to the formic acid source.

BRIEF SUMMARY OF THE INVENTION

It was an object of the present invention to provide a process for obtaining formic acid by thermal separation of a stream comprising formic acid and a tertiary amine, which has advantages over the prior art and which is capable of recovering formic acid in high yield, high concentration and high purity. Furthermore, the process should also be capable of being carried out in a manner which is as advantageous as possible with regard to energy and in particular should have economic advantages over the production processes of methyl formate hydrolysis which are currently carried out industrially. A low color number and a high color number stability are also of primary importance. Furthermore, the process should of course be capable of being carried out easily and should be reliable.

Accordingly, a process for obtaining formic acid by thermal separation of a stream comprising formic acid and a tertiary amine (I) was found, in which (a) a liquid stream comprising formic acid and a tertiary amine (I) in a molar ratio of from 0.5 to 5 is produced by combining tertiary amine (I) and a formic acid source;

from 10 to 100% by weight of the secondary components present in the liquid stream obtained from step (a) are separated from said liquid stream; and formic acid is removed by distillation in a distillation apparatus at a bottom temperature of from 100 to 300° C. and a pressure of from 30 to 3000 hPa abs from the liquid stream obtained from step (b);

and wherein the tertiary amine (I) used is an amine which has, at a pressure of 1013 hPa abs, a boiling point at least 5° C. higher than formic acid, in addition the tertiary amine (I) to be used in step (a) and the separation rate in the distillation apparatus mentioned in step (c) are chosen so that two liquid phases form in the bottom discharge of the distillation apparatus mentioned in step (c) under the conditions prevailing in step (d), (b) the bottom discharge from the distillation apparatus mentioned in step (c) is separated into two liquid phases, the upper liquid phase having a molar ratio of formic acid to tertiary amine (I) of from 0 to 0.5 and the lower liquid phase having a molar ratio of formic acid to tertiary amine (I) of from 0.5 to 5;

(c) the upper liquid phase of the phase separation is recycled from step (d) to step (a); and (d) the lower liquid phase of the phase separation is recycled from step (d) to step (b) and/or (c).

A BRIEF DESCRIPTION OF THE DRAWINGS

FIG. 1*a* shows a simplified block diagram of a general embodiment of the process according to the invention.

FIG. 1*b* shows a further simplified block diagram of a general embodiment of the process according to the invention.

Figure 11:
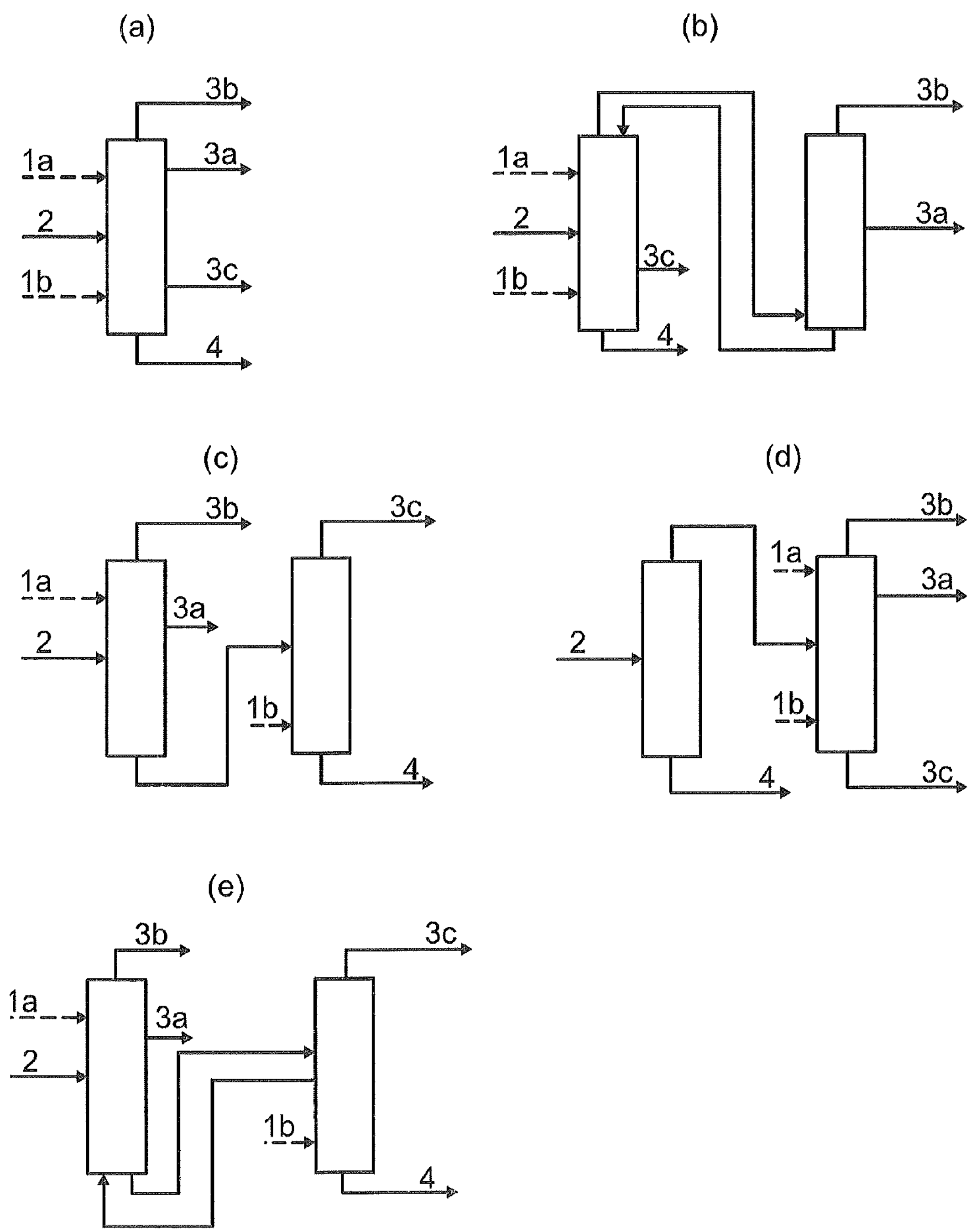

FIG. 11*a* shows a configuration having one distillation column.

FIGS. 11*b* to 11*e* show different configurations having two distillation columns.

Figure 12:
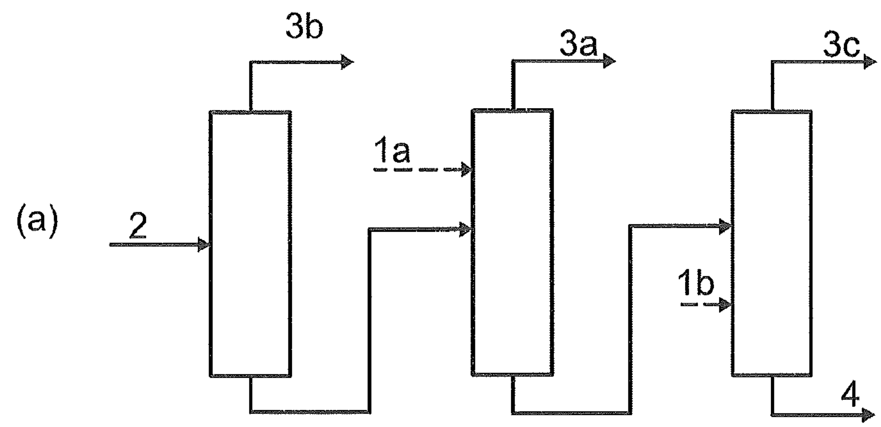
Figure 12:
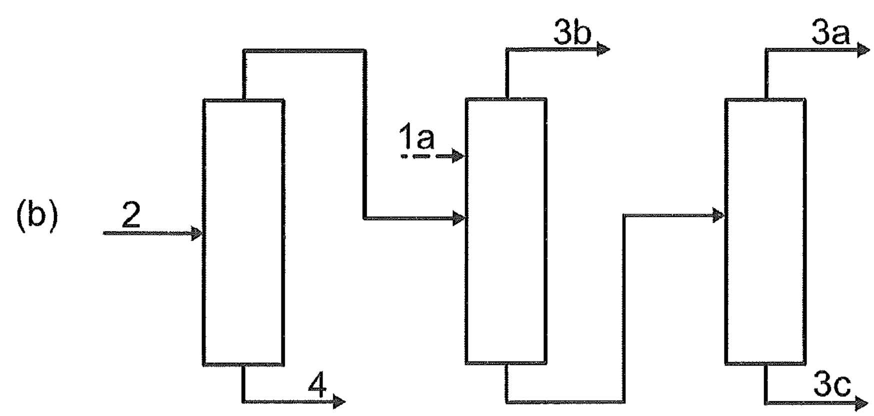
Figure 12:
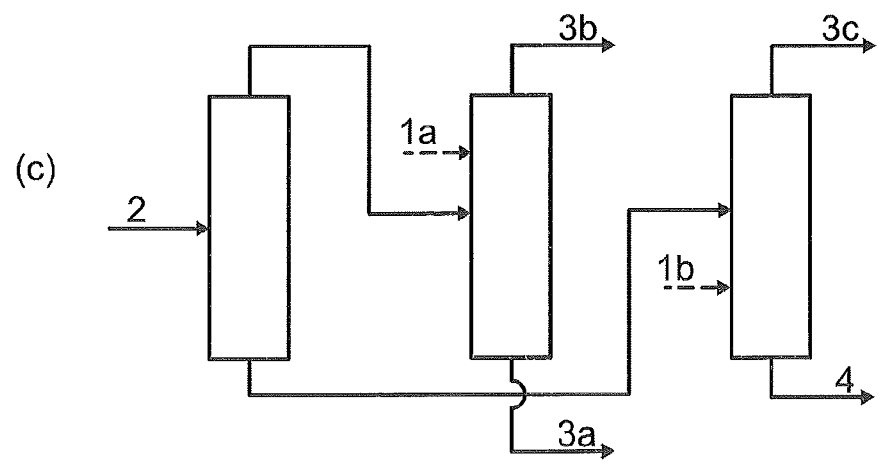

FIGS. 12*a* to 12*c* show different configurations having three distillation columns.

Figure 13:
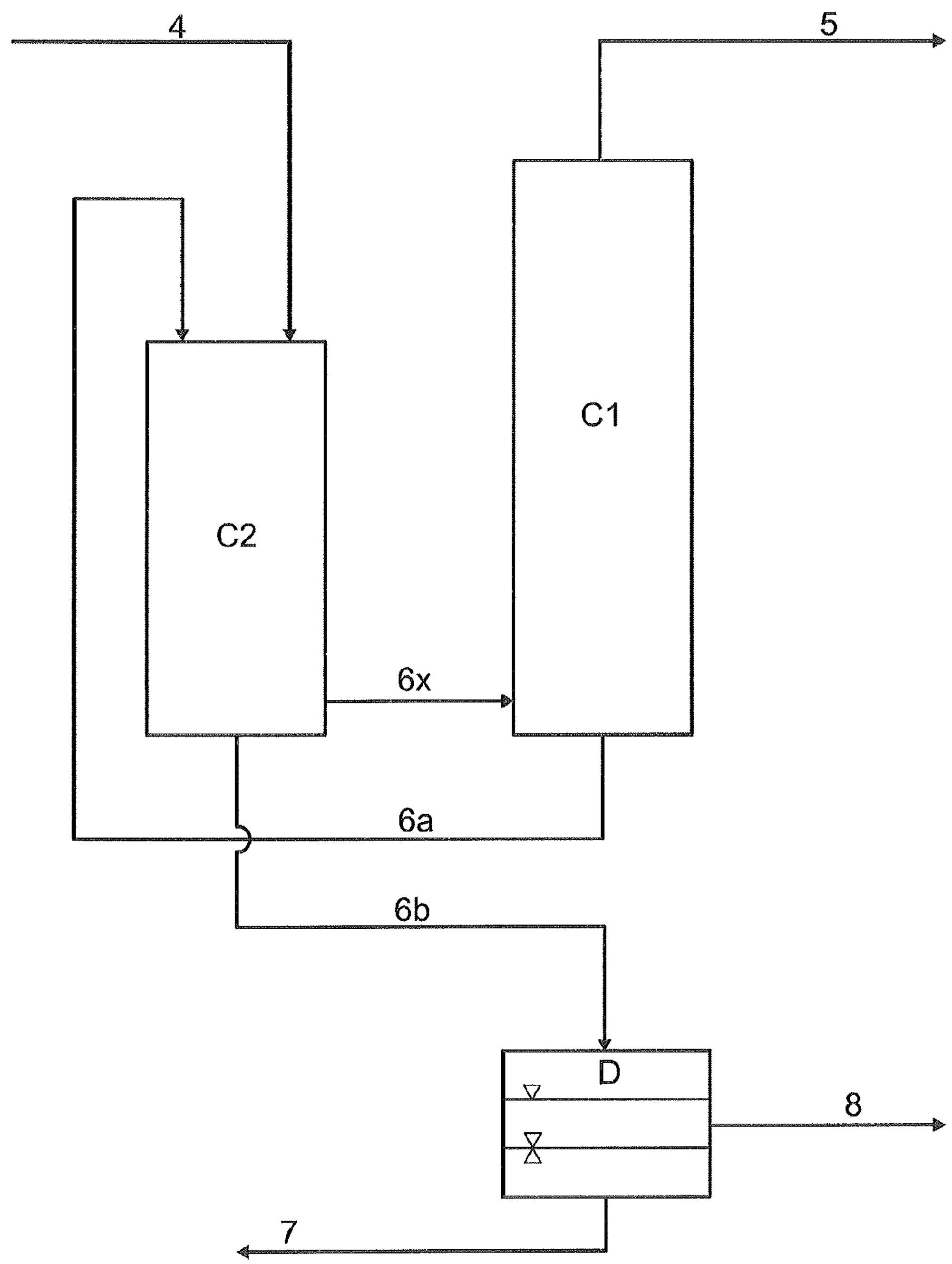

FIG. 13 shows laboratory plant 1 served for examination of steps (c) and (d) of the process according to the invention. The simplified block diagram of laboratory plant 1 is shown in FIG. 13.

Figure 14:
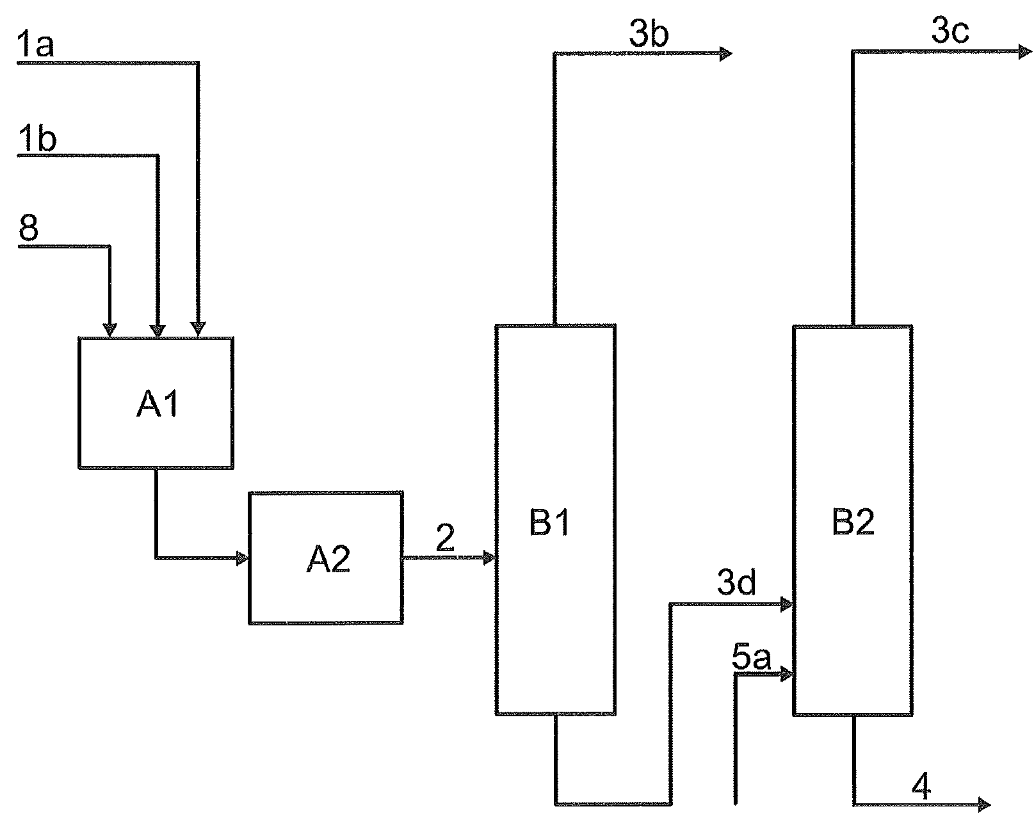

FIG. 14 shows the simplified block diagram of the laboratory plant 3.

DETAILED DESCRIPTION OF THE INVENTION

Formic acid source is to be understood as meaning the material stream which comprises formic acid in dilute, contaminated and/or chemically bound form or which comprises a precursor by means of which the formic acid is produced by chemical reaction. Dilute and/or contaminated formic acid may originate, for example, from various production processes or applications. It may be diluted, for example with water or organic solvents and contaminated with various other accompanying substances. For example, dilute, contaminated formic acid from the fermentation of renewable raw materials and aqueous formic acid from the methyl formate hydrolysis after removal of methanol and residual methyl formate may be mentioned as specific examples of this. The addition in chemically bound form can be effected, for example in the form of a complex, a salt or an addition compound between the formic acid and an amine other than the tertiary amine (I). Suitable chemical reactions are in principle all chemical reactions in which formic acid is produced. Of particular technical importance at the time of this patent application, however, are the production of the formic acid by hydrolysis of methyl formate and the production of the formic acid by transition metal-catalyzed hydrogenation of carbon dioxide. Both possible syntheses mentioned are well known among those skilled in the art and have been described previously in different variants and embodiments. A further technically relevant possibility for producing formic acid by chemical reaction is, for example, also the direct reaction of carbon monoxide with water.

In the case of the hydrolysis of methyl formate, usually methyl formate, water and tertiary amine (I) are introduced together or in succession into the hydrolysis reactor in order to trap the formic acid formed by the hydrolysis with the tertiary amine (I) in the form of an addition compound and thus to remove it from the hydrolysis equilibrium. As a result, a high conversion of methyl formate is achievable and particularly advantageous separation of the unreacted water by a subsequent distillation is possible.

In the case of the transition metal-catalyzed hydrogenation of carbon dioxide, the tertiary amine (I) is generally introduced into the hydrogenation reactor in order to form a stream comprising formic acid and a tertiary amine (I) in the hydrogenation itself.

The production of the stream comprising formic acid and tertiary amine (I) by hydrolysis of methyl formate in the presence of water and tertiary amine (I) is preferred in step (a). Further preferred in step (a) is the production of the stream comprising formic acid and tertiary amine (I) from dilute formic acid by concentration in the presence of tertiary amine (I). Particularly preferred in step (a), however, is the production of the stream comprising formic acid and tertiary amine (I) by hydrolysis of methyl formate in the presence of water and tertiary amine (I).

The liquid stream produced on combination of tertiary amine (I) and a formic acid source in step (a) has a molar ratio of formic acid to tertiary amine (I) of from 0.5 to 5. The molar ratio is preferably ≥1 and preferably ≤4 and particularly preferably ≤3. Said molar ratio is based on the total liquid stream, regardless of whether this is present in single-phase or multiphase form.

The liquid stream comprising formic acid and a tertiary amine (I) and produced in step (a) generally has a concentration of formic acid plus tertiary amine (I) of from 1 to 99% by weight, based on the total amount of the stream. Preferably, said stream has a concentration of formic acid plus tertiary amine (I) of ≥5% by weight and particularly preferably of ≥15% by weight and preferably of ≤95% by weight and particularly preferably of ≤90% by weight.

From 10 to 100% by weight of the secondary components present in the liquid stream obtained from step (a) are separated from said liquid stream. Said value range is based on the concentration of secondary components which the liquid stream produced in step (a) has. This concentration may be referred to below as "$c_{secondary\ components}$ (stream from step (a))". The liquid stream depleted in secondary components corresponds to the stream which, according to step (c), is fed to the distillation apparatus. This concentration may be referred to below as "$c_{secondary\ components}$ (feed stream to step (c))". Thus, the abovementioned separation of secondary components is based on the quotient $$\frac{c_{secondary\ components}(\text{feed stream to step } (c))\ [\text{g/L}]}{c_{secondary\ components}(\text{stream from step } (a))\ [\text{g/L}]} \cdot 100\% \text{ by weight.}$$

Preferably ≥20% by weight and particularly preferably ≥30% by weight and preferably ≤99.99% by weight and particularly preferably ≤99.9% by weight of the secondary components are separated off in step (b).

The term secondary components is to be understood as meaning all the components which are present in the liquid stream obtained in step (a) and which are neither formic acid nor tertiary amine (I). Water, methanol (in particular in the hydrolysis of methyl formate), dissolved unhydrolyzed methyl formate (in particular in the hydrolysis of methyl formate), possible degradation products of the tertiary amine (I), dissolved inert gases, homogeneous catalyst (in particular in the hydrogenation of carbon dioxide), dissolved carbon dioxide or dissolved hydrogen (in particular in the hydrogenation of carbon dioxide), solvent and other components may be mentioned as examples.

The manner in which the secondary components are separated off is unimportant for the process according to the invention. Thus, for example, customary and known methods for separating liquid mixtures of substances can be used. First and foremost, the distillative separation may be mentioned here. In this, the liquid mixture of substances is separated in a distillation apparatus. Thus, for example, low-boiling secondary components, such as, for example, methanol, methyl formate or water, can be separated off via the top or as a side take-off. However, it is also conceivable to separate off high-boiling secondary components via the bottom and the mixture comprising formic acid and tertiary amine (I) as a side stream or top product. In addition to the distillative separation, however, membrane, absorption, adsorption, crystallization, filtration, sedimentation or extraction methods are also possible. Extraction methods are preferred in the concentration of dilute aqueous formic acid and the use of tertiary amines (I) which are immiscible or miscible only to a small extent with water.

It is of course also possible to combine a plurality of separation steps which furthermore may also be based on different methods. The design of the separation step or of the separation steps' can be carried out using the customary technical knowledge.

In the process according to the invention, it is of course possible to carry out still further process steps in addition to step (b) between the steps (a) and (c).

Formic acid is removed by distillation in a distillation apparatus at a bottom temperature of from 100 to 300° C. and a pressure of from 30 to 3000 hPa abs from the liquid stream obtained from step (b).

The distillation apparatus comprises, in addition to the actual column body with internals, inter alia a top condenser and a bottom evaporator. In addition, this may optionally also comprise still further peripheral apparatuses or internals and, for example, a flash container in the feed (for example for separating gas and liquid in the feed to the column body), an intermediate evaporator (for example for improved heat integration of the process) or internals for avoiding or reducing aerosol formation (such as, for example, thermostatable trays, demisters, coalescers or deep-bed diffusion filters). The column body may be equipped, for example, with structured packings, random packings or trays. The number of separation stages required is dependent in particular on the type of tertiary amine (I), the concentration of formic acid and tertiary amine (I) in the feed of the distillation apparatus in step (c) and the desired concentration or the desired purity of the formic acid and can be determined by the person skilled in the art in the customary manner. In general, the number of required separation stages is ≥3, preferably ≥6 and particularly preferably ≥7. There are in principle no upper limits. For practical reasons, however, it is likely to be customary to use as a rule ≤50, optionally ≤30, separation stages.

The stream comprising formic acid and a tertiary amine (I) and obtained from step (b) can be fed to the distillation apparatus, for example, as a side stream to the column body.

Optionally, the addition can also be effected upstream of a flash evaporator, for example. In order to keep the thermal load on the feed stream in the distillation apparatus as low as possible, it is generally advantageous rather to feed this to the lower region of the distillation apparatus. Thus, it is preferable in step (c) to feed in the stream comprising formic acid and a tertiary amine (I) in the region of the lower fourth, preferably in the region of the lower fifth and particularly preferably in the region of the lower sixth of the available separation stages, a direct feed into the bottom of course also being included here.

Alternatively, however, it is also preferable in step (c) to feed said stream from step (b) comprising formic acid and a tertiary amine (I) to the bottom evaporator of the distillation apparatus.

The distillation apparatus is operated at a bottom temperature of from 100 to 300° C. and a pressure of from 30 to 3000 hPa abs. Preferably, the distillation apparatus is operated at a bottom temperature of ≥120° C., particularly preferably of ≥140° C. and preferably of ≤220° C. and particularly preferably of ≤200° C. The pressure is preferably ≥30 hPa abs, particularly preferably ≥60 hPa abs and preferably ≤1500 hPa abs and particularly preferably ≤500 hPa abs.

Depending on composition and origin of the formic acid and a feed comprising tertiary amine (I) to the distillation apparatus, formic acid can be obtained as top product and/or side product from the distillation apparatus. When the feed comprises constituents boiling lower than formic acid, it may be advantageous to separate these off by distillation as top product and the formic acid in the side take-off. Where gases may be dissolved in the feed (such as, for example, carbon monoxide or carbon dioxide), however, it is as a rule also possible to separate off the formic acid together with these as top product. If the feed comprises constituents boiling higher than formic acid, formic acid is preferably separated off by distillation as top product, but optionally instead of these or in addition in the form of a second stream in the side take-off. The constituents boiling higher than formic acid are in this case then preferably taken off via an additional side stream. The side stream with secondary components can optionally be returned to step (b) to remove the secondary components.

In this way, formic acid having a content of up to 100% by weight can be obtained. In general, formic acid contents of from 75 to 99.995% by weight are achievable without problems. The residual content to 100% by weight is mainly water, other components, such as, for example, solvents or possible decomposition products of course also being conceivable, according to the substances introduced into the distillation apparatus in addition to formic acid and the tertiary amine (I). Thus, water may, for example, already be present in the feed of the distillation apparatus but may optionally also form only during the thermal separation in small amounts as a result of decomposition of formic acid itself.

In the recovery of concentrated formic acid having a content from 95 to 100% by weight as bottom or side product, water is discharged with a part of the eliminated formic acid in a side stream. The formic acid content of this side stream is typically from 75 to 95% by weight. However, it is also possible to discharge the water and the eliminated formic acid in a common top or side stream. The formic acid content of the product thus obtained is then as a rule from 85 to 95% by weight. The aqueous formic acid from the side stream can optionally be returned to step (b) to remove the water.

Furthermore, it was recognized according to the invention that an oxidative degradation of the tertiary amine (I) can occur as a result of the presence of oxygen and it is therefore particularly advantageous, especially on operation of the distillation apparatus at pressures below 0.1 MPa abs, to avoid or at least keep extremely low the introduction of oxygen through as small a number as possible of connections, nozzles and flanges, by particular care in the installation, by use of particularly tight flange connections (for example those having chamber profile seals or weld lip seals) or by nitrogen-blanketed flange connections. A suitable flange connection is disclosed, for example, in DE 10 2009 046 310 A1.

The formic acid obtainable by the process according to the invention has a low color number and a high color number stability. In general, a color number of ≤20 APHA and in particular even of ≤10 APHA and optionally even of ≤5 APHA can be achieved without problems. Even on storage for several weeks, the color number remains virtually constant or increases only insignificantly.

Furthermore, in spite of the theoretically possible formation of secondary components, such as, for example, aldehydes, carboxylic acids, alcohols, alkyl formates or formamides, from the cleavage of the tertiary amine (I), the content of such secondary components in the formic acid obtainable is ≤100 ppm by weight, preferably ≤50 ppm by weight and very particularly preferably ≤25 ppm by weight.

As the case may be, it may also be advantageous to use a plurality of distillation apparatuses in step (c), in particular if, in addition to the free formic acid and the amine (I)-containing bottom product, still further fractions, for example comprising accompanying substances, byproducts of the reaction, impurities and/or formic acid fractions of different purities and concentrations, are to be recovered.

The distillation apparatus for separating off the formic acid can of course also be designed as thermally coupled distillation columns or as a dividing wall column.

The tertiary amine (I) to be used in the process according to the invention has, at a pressure of 1013 hPa abs, a boiling point at least 5° C. higher than formic acid. Preferably, the tertiary amine (I) to be used has a boiling point at least 10° C., particularly preferably a boiling point at least 50° C. and very particularly preferably a boiling point at least 100° C. higher than formic acid. A limitation with regard to an upper limit for the boiling point is not required since a vapor pressure of the tertiary amine (I) which is as low as possible is in principle advantageous for the process according to the invention. In general, the boiling point of the tertiary amine (I) is below 500° C. at a pressure optionally extrapolated by known methods from a vacuum to 1013 hPa abs.

In addition, the tertiary amine (I) to be used in step (a) and the separation rate in the distillation apparatus mentioned in step (c) are chosen so that two liquid phases form in the bottom discharge of the distillation apparatus mentioned in step (c) under the conditions prevailing in step (d).

The formation of two liquid phases is mainly determined by the chemical and physical properties of the two phases. These in turn can be influenced by the choice of the tertiary amine (I) to be used, by the separation rate in the distillation apparatus, but also by the presence of any additional components, such as, for example, of solvents, and the concentrations thereof.

The separation rate is to be understood as meaning the quotient $$\frac{m_{formic\ acid}(\text{feed stream to step }(c))\ [\text{g/h}] - m_{formic\ acid}(\text{bottom discharge})\ [\text{g/h}]}{m_{formic\ acid}(\text{feed stream to step }(c))\ [\text{g/h}]}\cdot 100\%$$

"$m_{formic\ acid}$ (feed stream to step (c))" corresponding to the amount of formic acid fed per unit time to the distillation apparatus and "$m_{formic\ acid}$ (bottom discharge)" corresponding to the amount of formic acid removed per unit time via the bottom discharge. In the process according to the invention, a separation rate of in general ≥10%, preferably ≥25% and particularly preferably ≥40% and in general of ≤99.9%, preferably ≤99.5% and particularly preferably ≤99.0% is chosen. The separation rate can be influenced, for example, simply by the temperature and pressure conditions in the distillation apparatus and by the residence time in the distillation apparatus. It can be determined by simple experiments, optionally also during the operation of the process according to the invention.

The suitability of a tertiary amine (I) or of any additionally desired solvent can be determined, for example, in simple experiments in which the phase properties are determined under the intended conditions.

In step (d), the bottom discharge from the distillation apparatus mentioned in step (c) is separated into two liquid phases, the upper liquid phase having a molar ratio of formic acid to tertiary amine (I) of from 0 to 0.5 and the lower liquid phase having a molar ratio of formic acid to tertiary amine (I) of from 0.5 to 5.

The phase separation can be effected, for example, in a separate phase separator which is downstream of the distillation apparatus. However, it is also possible to integrate the phase separator in the bottom region of the distillation apparatus, in the region of the bottom evaporator or in the region of the bottom evaporator circulation. For example, the use of a centrifugal separator is also possible or optionally even advantageous here.

Since the formation of two liquid phases is influenced not only by the chemical and physical properties of the two phases but also by the temperature, as a rule the miscibility increasing with the temperature, it may optionally be advantageous for improving the phase separation to operate this at a lower temperature than the bottom temperature chosen beforehand. For this purpose, the bottom discharge is usually cooled to a temperature in the range from 30 to 180° C. in an intermediate heat exchanger. The phase separation is preferably effected at a temperature of ≥50° C. or at a temperature of ≤160° C.

The upper liquid phase in step (d) has a molar ratio of formic acid to tertiary amine (I) of preferably ≥0.005 and particularly preferably ≥0.015 and preferably ≤0.25 and particularly preferably ≤0.125. The lower liquid phase in step (d) has a molar ratio of formic acid to tertiary amine (I) of preferably ≥0.75 and particularly preferably ≥1 and preferably ≤3.5 and particularly preferably ≤3.

Furthermore, it is advantageous in the process according to the invention to choose the separation rate in the distillation apparatus mentioned in step (c) so that the molar ratio of formic acid to tertiary amine (I) in the bottom discharge is from 0.1 to 2.0. Bottom discharge is to be understood as meaning the totality of the liquid bottom condensates which leave the distillation apparatus and, according to step (d), are separated into two liquid phases. It is unimportant whether the bottom condensates originate, for example, directly from the bottom of the distillation apparatus itself, the bottom of the bottom evaporator or, for example, from both. Preferably, the separation rate in the distillation apparatus mentioned in step (c) is chosen so that the molar ratio of formic acid to tertiary amine (I) in the bottom discharge is preferably ≤1.5.

In the process according to the invention, according to step (e), the upper liquid phase of the phase separation is recycled from step (d) to step (a). As a result, the tertiary amine (I) present in the upper liquid phase can be used, by the combination with the formic acid source, for further production of a stream comprising formic acid and tertiary amine (I). In general, from 10 to 100%, preferably from 50 to 100%, particularly preferably from 80 to 100%, very particularly preferably from 90 to 100% and in particular from 95 to 100% of the upper liquid phase are recycled to step (a).

In the case of the hydrolysis of methyl formate, the upper liquid phase is preferably recycled directly to the hydrolysis stage.

It is of course also possible to integrate further process steps in the recycling of the upper liquid phase. Purification of the upper liquid phase to be recycled or of the tertiary amine (I) present therein to remove undesired accompanying substances, byproducts of the reaction or impurities may be mentioned, for example, as a nonlimiting example. In principle, there are also no limits with regard to the type of intermediate process steps. It is also possible to specifically remove a part of the upper liquid phase as so-called purge stream. Lacking or lost amounts of tertiary amine (I) can of course be replenished by freshly added tertiary amine (I), it being possible for this to be fed in, for example, via the recycle stream or directly to step (a).

In the process according to the invention, according to step (f), the lower liquid phase of the phase separation is recycled from step (d) to step (b) and/or (c). As a result, the formic acid present in the lower liquid phase can likewise be used for obtaining formic acid by distillative separation. Depending on the desired embodiment, in the process according to the invention the lower liquid phase can thus be recycled (i) to step (b), (ii) split between steps (b) and (c) or (iii) recycled to step (c). In general, however, the recycling to step (c) is preferred since the load on the lower liquid phase comprising formic acid and tertiary amine (I) is usually lowest thereby and the material stream in step (b) is not increased in quantity, which would otherwise have resulted in correspondingly larger dimensioning. In general, from 10 to 100%, preferably from 50 to 100%, particularly preferably from 80 to 100%, very particularly preferably from 90 to 100% and in particular from 95% to 100% of the lower liquid phase are recycled to step (b) and/or (c).

In the present invention, however, it is also possible to recycle a further part to step (a) in addition to said recycling of the lower liquid phase to step (b) and/or (c). It is advantageous, for example, in the case of the production of the formic acid by transition metal-catalyzed hydrogenation of carbon dioxide, since this as a rule is effected in the presence of a polar solvent which may likewise become enriched in the lower liquid phase and can therefore be recycled to step (a).

Of course, still further process steps can also be integrated in the recycling of the lower liquid phase. A purification of the lower liquid phase to be recycled or of the tertiary amine (I) present therein and/or of the formic acid present therein to remove undesired accompanying substances, byproducts of the reaction or impurities may also be mentioned here as a nonlimiting example. In principle, there are also no limits also with regard to the type of intermediate process steps. It is also possible to remove a part of the lower liquid phase in a targeted manner as so-called purge stream in order thus to remove undesired byproducts or impurities.

According to the invention, it was recognized that, in the recovery of formic acid by thermal separation of a stream comprising formic acid and an amine, metals and metal compounds dissolve as a result of slight surface corrosion which is virtually unavoidable in the case of the customary materials and enter the liquid material streams. The dissolved metals and/or metal compounds become distributed over the process streams in the entire plant, become concentrated and, on exceeding the solubility limits, accumulate in an uncontrolled manner at various points, such as, for example, at flowmeters, control valves, pumps, heat exchanger surfaces and the inner surfaces of containers (such as, for example, in the bottom region of distillation apparatuses). This may in the long term result in serious problems in the operation of the plant. Apart from direct damage to the affected plant parts, frequent shutdown of the plant for cleaning the affected apparatuses may result in a loss of production capacity. In order to avoid this from the outset, it would of course be possible to construct the plant from more noble materials. However, this would be very complicated and expensive.

In the process according to the invention, it was recognized that the dissolved metals and metal compounds accumulate in polar liquid phases, in particular in the lower liquid phase formed according to step (d). Furthermore, it was recognized that it was advantageous to remove the metals and metal compounds from the lower liquid phase formed according to step (d). The upper phase which was formed according to step (d) and is recycled to step (a) is virtually free of metals and metal compounds. This prevents the dissolved metals and metal compounds from becoming distributed via recycle process streams in the entire plant and causing the problems described above. The manner of removal of the metals and metal compounds is in principle not limited. It is possible, for example, to remove these via a so-called purge stream. The simplest removal is the concentration of the metal compounds above the solubility limit and the discharge as solid, for example from the phase separation vessel in step (d). In order to be able to recover the formic acid present therein and the tertiary amine (I) present therein and to recycle them, it may be advantageous to subject the discharged purge stream to evaporation, preferably under reduced pressure. Formic acid and tertiary amine (I) would evaporate off and could then be recovered by condensation. The metals and metal compounds would remain behind as residue on evaporation. Partial evaporation, for example, of the formic acid to reduce the solubility and subsequent filtering off of the precipitated metals and metal compounds would also be conceivable. Further possibilities for removing the metals and metal compounds from the lower liquid phase consist in removing them from the discharged purge stream, for example by washing with an alkali, by adsorption on suitable adsorbents or by treatment with an ion exchanger. For example, commercially available activated carbons, silica gels, zeolites, molecular sieves, aluminum oxides and ion exchange resins having various functional groups, such as $—SO_3H$, $—CO_2H$, $—NR^1R^2$ ($R^1$, $R^2$ for example are H, alkyl, $—CH_2CO_2H$, $—CH_2PO_3H_2$, —C(SH)NH), $—PO_3H_2$, —SH), may be mentioned as suitable adsorbents. In principle, said measures can of course be carried out not only with a discharged purge stream but also with the total liquid stream. However, owing to the larger liquid stream, this will be much more complicated, so that as a rule the removal from a purge stream is preferable.

The tertiary amine (I) preferably to be used in the process according to the invention has the general formula (Ia)

$$NR^1R^2R^3 \tag{Ia},$$

in which the radicals $R^1$ to $R^3$ are identical or different and, independently of one another, are a straight-chain or branched, acyclic or cyclic, aliphatic, araliphatic or aromatic radical having in each case 1 to 16 carbon atoms, preferably 1 to 12 carbon atoms, it also being possible for individual carbon atoms, independently of one another, to be substituted by a heterogroup selected from the group consisting of —O— and >N— and it being possible for two or all three radicals also to be linked to one another with the formation of a chain comprising at least four atoms in each case.

For example, the following are mentioned as suitable amines:

Tri-n-propylamine (b.p.$_{1013\ hPa}$=156° C.), tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine.

Dimethyldecylamine, dimethyldodecylamine, dimethyltetradecylamine, ethyldi(2-propyl)amine (b.p.$_{1013\ hPa}$=127° C.), dioctylmethylamine, dihexylmethylamine.

Tricyclopentylamine, tricyclohexylamine, tricycloheptylamine, tricyclooctylamine and the derivatives thereof substituted by one or more methyl, ethyl, 1-propyl, 2-propyl, 1-butyl, 2-butyl or 2-methyl-2-propyl groups.

Dimethylcyclohexylamine, methyldicyclohexylamine, diethylcyclohexylamine, ethyldicyclo-hexylamine, dimethylcyclopentylamine, methyldicyclopentylamine.

Triphenylamine, methyldiphenylamine, ethyldiphenylamine, propyldiphenylamine, butyl-diphenylamine, 2-ethylhexyldiphenylamine, dimethylphenylamine, diethylphenylamine, dipropylphenylamine, dibutylphenylamine, bis(2-ethylhexyl)phenylamine, tribenzylamine, methyldibenzylamine, ethyldibenzylamine and the derivatives thereof substituted by one or more methyl, ethyl, 1-propyl, 2-propyl, 1-butyl, 2-butyl or 2-methyl-2-propyl groups.

N—$C_1$— to $C_{12}$-alkylpiperidines, N,N-di-$C_1$— to $C_{12}$-alkylpiperazines, N—$C_1$— to $C_{12}$-alkyl-pyrrolidines, N—$C_1$— to $C_{12}$-alkylimidazoles and the derivatives thereof substituted by one or more methyl, ethyl, 1-propyl, 2-propyl, 1-butyl, 2-butyl or 2-methyl-2-propyl groups.

1,8-Diazabicyclo[5.4.0]undec-7-ene ("DBU"), 1,4-diazabicyclo[2.2.2]octane, N-methyl-8-azabicyclo[3.2.1]octane ("tropane"), N-methyl-9-azabicyclo[3.3.1]nonane ("granatane"), 1-azabicyclo[2.2.2]octane ("quinuclidine"), 7,15-diazatetracyclo[7.7.1.$0^{2,7}0^{10,15}$]heptadecane ("sparteine").

In the process according to the invention, it is of course also possible to use mixtures of different tertiary amines (I). Of course, all tertiary amines (I) used then preferably have a boiling point at least 5° C. higher than formic acid at a pressure of 1013 hPa abs.

Among the above-described tertiary amines of the general formula (Ia), those in which the radicals $R^1$ to $R^3$ are identical or different and, independently of one another, are a straight-chain or branched, acyclic or cyclic, aliphatic, araliphatic or aromatic radical having in each case 1 to 16 carbon atoms, preferably 1 to 12 carbon atoms, are in turn preferred, it being possible for individual carbon atoms, independently of one another, also to be substituted by a heterogroup selected from the group consisting of —O— and >N— and it also being possible for two or all three radicals to be linked to one another with the formation of a saturated chain comprising at least four atoms in each case.

Preferably, at least one of the radicals on the alpha-carbon atom carries two hydrogen atoms.

In the process according to the invention, an amine of general formula (Ia) in which the radicals $R^1$ to $R^3$, independently of one another, are selected from the group consisting of $C_1$— to $C_{12}$-alkyl, $C_5$- to $C_8$cycloalkyl, benzyl and phenyl is particularly preferably used as tertiary amine (I).

In the process according to the invention, a saturated amine of the general formula (Ia) is particularly preferably used as tertiary amine (I).

In the process according to the invention, an amine of the general formula (Ia) in which the radicals $R^1$ to $R^3$, independently of one another, are selected from the group consisting of $C_5$— to $C_8$-alkyl, in particular tri-n-pentylamine, tri-n-hexylamine, tri-n-heptylamine, tri-n-octylamine, dimethylcyclohexylamine, methyldicyclohexylamine, dioctylmethylamine and dimethyldecylamine is very particularly preferably used as tertiary amine (I).

The streams formed in the process according to the invention and comprising formic acid and tertiary amine (I) may, in addition to the free formic acid and the free tertiary amine (I) as a mixture, comprise the formic acid and the tertiary amine (I) also in various other forms. The type and amount of the individual forms may differ depending on the prevailing conditions, such as for example, the relative ratios of formic acid to tertiary amine (I), the presence of further components (for example water, solvent, byproducts, impurities) and hence in the end also the concentration of formic acid and tertiary amine (I), the temperature and the pressure. Thus, the following conceivable forms may be mentioned by way of example:

Ammonium formate (molar ratio of formic acid to tertiary amine (I) of 1) or formic acid-rich adduct with the tertiary amine (I) (molar ratio of formic acid to tertiary amine (I) of >1).

Ionic liquid.

The type and amount of the individual forms are unimportant for carrying out the process according to the invention.

The liquid stream from step (b) to be recycled to step (c) may of course also comprise still further components, such as, for example, secondary components which were not separated off or not completely separated off in step (b), in addition to formic acid and tertiary amine (I). In addition to formic acid and tertiary amines (I), preferably only those components which can also be separated from the formic acid by distillation in step (c) without problems or at least can be easily separated from the resulting formic acid in a downstream step, for example, by a subsequent distillation, extraction, absorption or adsorption, should be recycled to step (c).

The concentration of possible further components in addition to formic acid and tertiary amine (I) in the liquid stream to be recycled to step (c) and the content of formic acid and tertiary amine (I) present in the stream are in principle unimportant for carrying out the process according to the invention. However, owing to the efficiency of the process according to the invention, it is advantageous not to recycle the formic acid and the tertiary amine (I) in too great a dilution to step (c), since as a rule the dilution does of course also affect the size and design of the distillation apparatus and the energy consumption thereof. In general, it is therefore advisable to recycle a stream having a total content of at least 10% by weight, preferably at least 50% by weight and particularly preferably at least 80% by weight of formic acid and tertiary amine (I).

The liquid stream to be recycled to step (c) from step (b) may optionally also comprise so-called solvents.

If a solvent is to be used, it is in general advantageous for this to be immiscible or only insignificantly miscible with the tertiary amine (I) but readily miscible with formic acid and therefore rather to be present in the lower liquid phase in step (d). An electrostatic factor, also abbreviated to EF, of preferably $\geq 200 \cdot 10^{-30}$ Cm has proved to be a measure for this purpose. The electrostatic factor EF is defined as the product of the relative dielectric constant $\epsilon_r$ and the dipole moment $\mu$ of the solvent (see, for example, C. Reichardt, "Solvents and Solvent Effects in Organic Chemistry", 3rd edition, Wiley-VCH Verlag GmbH & Co KGaA, Weinheim 2003, Chapter 3.2, bottom of page 67 to top of page 68). This preferred value ensures that the optional solvent has a certain minimum polarity and is miscible with the lower liquid phase in step (d).

The use of solvents can, for example, improve the separation of the two liquid phases, dependent on the respective system (for example type of tertiary amine (I), concentrations, temperature, pressure and the like).

Classes of substances which are particularly suitable as optional solvent are in particular diols and their formic esters, polyols and their formic esters, sulfones, sulfoxides, open-chain or cyclic amides and mixtures of said classes of substances.

For example, ethylene glycol (EF=$290.3 \cdot 10^{-30}$ Cm), diethylene glycol (EF=$244.0 \cdot 10^{-30}$ Cm), triethylene glycol, polyethylene glycol, 1,3-propanediol (EF=$285.6 \cdot 10^{-30}$ Cm), 2-methyl-1,3-propanediol, 1,4-butanediol (EF=$262.7 \cdot 10^{-30}$ Cm), dipropylene glycol, 1,5-pentanediol (EF=$212.5 \cdot 10^{-30}$ Cm), 1,6-hexanediol and glycerol may be mentioned as suitable diols and polyols. Owing to their OH groups, diols and polyols can be esterified in the presence of formic acid. In the process according to the invention, this is effected in particular in step (c) in the thermal separation of the stream comprising formic acid and tertiary amine (I) in the said distillation apparatus. Since the resulting formic esters show very similar phase behavior, they are generally also suitable as solvents. Also, the water forming during the esterification is harmless in the thermal separation. There is no increase in the amount of water in the continuous operation of the process according to the invention since water in these small amounts can be separated off in the distillation apparatus via a side take-off.

For example, dialkyl sulfoxides, preferably $C_1$— to $C_6$-dialkyl sulfoxides, in particular dimethyl sulfoxide (EF=$627.1\cdot10^{-30}$ Cm), are mentioned as suitable sulfoxides.

For example, formamide (EF=$1243.2\cdot10^{-30}$ Cm), N-methylformamide (EF=$2352.9\cdot10^{-30}$ Cm), N,N-dimethylformamide (EF=$396.5\cdot10^{-30}$ Cm), N-methylpyrrolidone (EF=$437.9\cdot10^{-30}$ Cm), acetamide and N-methylcaprolactam are mentioned as suitable open-chain or cyclic amides.

As the case may be, however, it may also be advantageous to use just one preferably nonpolar solvent with $<200\times10^{-30}$ Cm. Nonpolar solvents may optionally reduce the concentration of formic acid in the upper liquid phase.

However, the process according to the invention is preferably carried out without addition of a solvent.

Figure 1A:
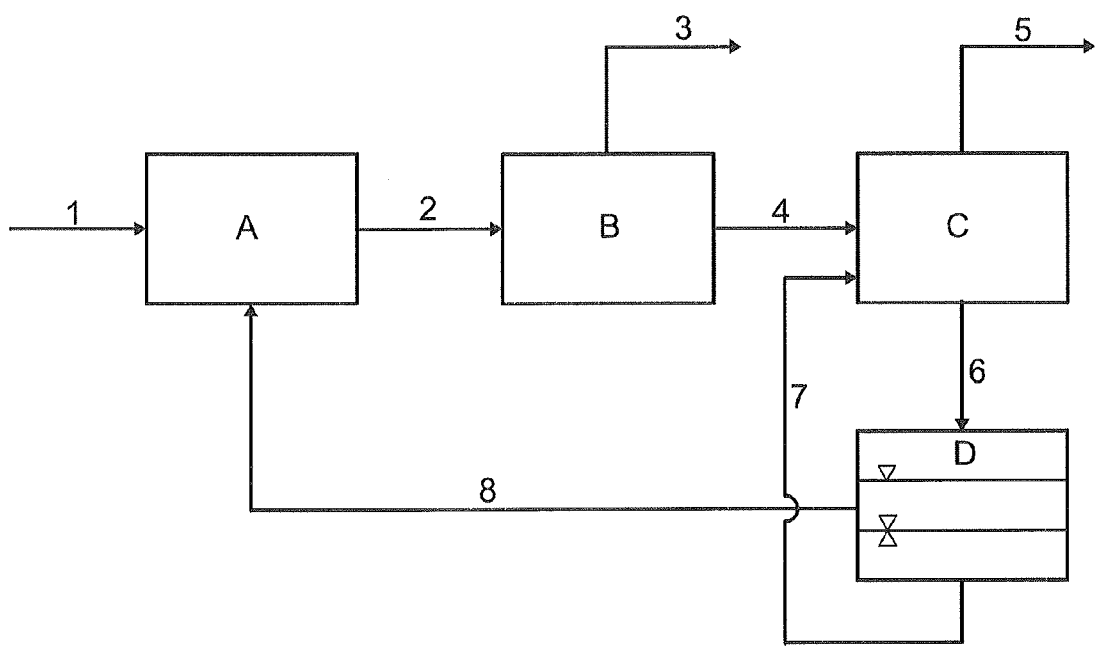

FIG. 1*a* shows a simplified block diagram of a general embodiment of the process according to the invention. There, individual letters have the following meaning:

A=Apparatus for producing a stream comprising formic acid and tertiary amine (I)

B=Apparatus for separating off secondary components

C=Distillation apparatus

D=Phase separation vessel

A formic acid source is fed via stream (1) and tertiary amine (I) via stream (8) to the apparatus A for producing a stream comprising formic acid and tertiary amine (I). As already explained further above, the formic acid source to be fed in can, for example, already comprise formic acid in dilute, contaminated and/or chemically bound form or can comprise a precursor by means of which formic acid is produced by chemical reaction. The stream (2) comprising formic acid and tertiary amine (I) is taken off from apparatus A and fed to the apparatus B for separating off secondary components. Said apparatus B may be, for example, a distillation apparatus in which low-boiling secondary components can be removed by distillation. The secondary components separated off are removed via stream (3). The stream concentrated with respect to formic acid and tertiary amine (I) is fed via stream (4) to the distillation apparatus C. Formic acid is separated off there by distillation as stream (5). The bottom product of the distillation apparatus C is fed as stream (6) to the phase separation vessel D for phase separation. The upper liquid phase is recycled as stream (8) to the apparatus A. The lower liquid phase is recycled as stream (7) to the distillation apparatus C.

Figure 1B:
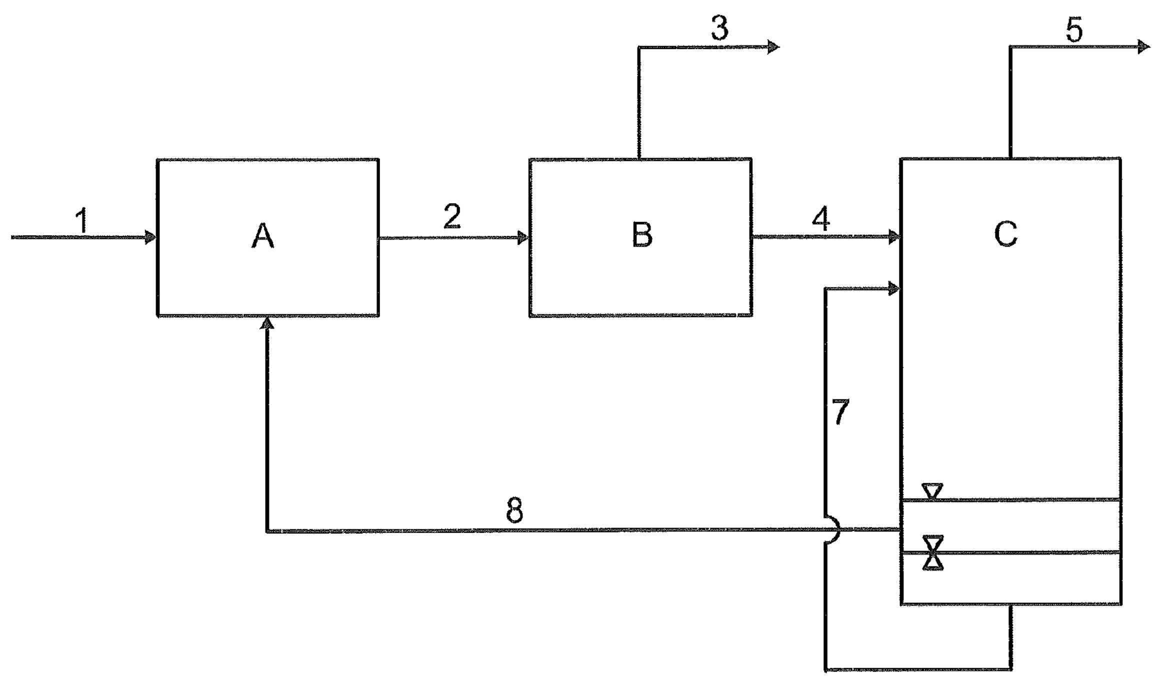

FIG. 1*b* shows a further simplified block diagram of a general embodiment of the process according to the invention. There, the individual letters have the following meaning:

A=Apparatus for producing a stream comprising formic acid and tertiary amine (I)

B=Apparatus for separating off secondary components

C=Distillation apparatus with integrated phase separation

The process according to FIG. 1*b* corresponds substantially to the process according to FIG. 1*a* but with the difference that the phase separation is integrated into the distillation apparatus C. The formic acid is separated off from the distillation apparatus C likewise as stream (5). The upper liquid phase is recycled as stream (8) to the apparatus A. The lower liquid phase is recycled as stream (7) to the distillation apparatus C.

In the process according to the invention, various configurations are possible in the region of the distillation apparatus C and of the phase separation D. They differ not only in whether the phase separation takes place in a separate container or is integrated in the bottom of the distillation column but also in the site of the addition of the stream comprising formic acid and tertiary amine (I) to the distillation apparatus and in the flow path between the column container and the bottom evaporator and the point of removal of the bottom discharge.

Figure 2:
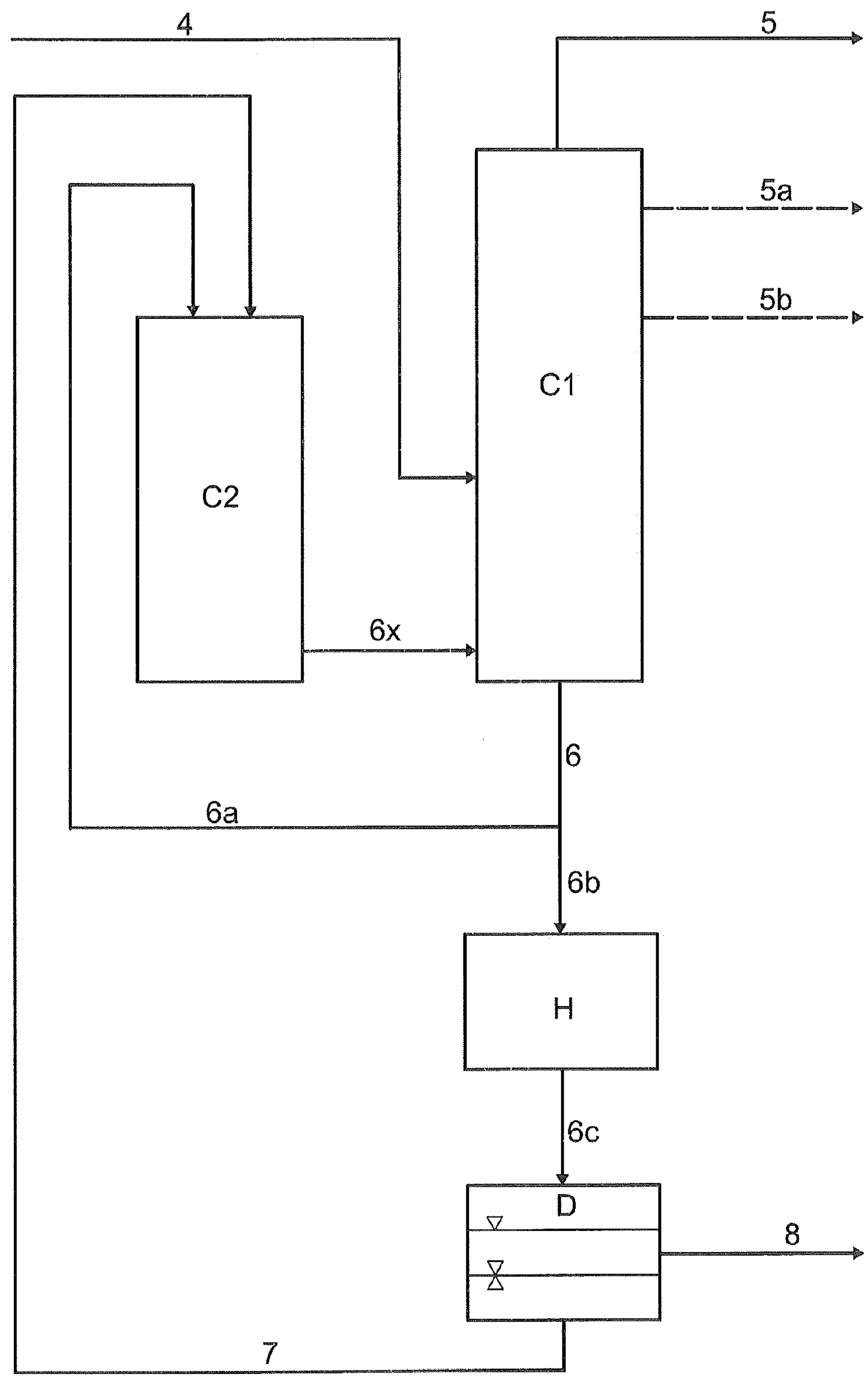
FIG. 2 shows a simplified block diagram of a configuration preferred in the process according to the invention, in the region of the distillation apparatus C and of the phase separation D.

FIG. 2 shows a simplified block diagram of a configuration preferred in the process according to the invention, in the region of the distillation apparatus C and of the phase separation D. There, the individual letters have the following meaning:

C1=Column body with internals

C2=Bottom evaporator

D=Phase separation vessel

H=Heat exchanger

Stream (4) comprising formic acid and tertiary amine (I) is fed to the column body C1. Depending on composition and origin of the feed comprising formic acid and a tertiary amine (I) to the distillation apparatus C, the formic acid is removed by distillation as top product via stream (5), as side product via stream (5*a*) and/or as side product via stream (5*b*), in particular the three following variants being followed.

The first variant plays a role as a rule when secondary components which boil lower than formic acid are still present in the feed to the distillation apparatus C. Said secondary components are then separated off as stream (5). The formic acid (for example having a formic acid content of up to 100% by weight) is then separated off via stream (5*a*). As a rule, water-containing formic acid (for example having a formic acid content of from 75 to 95% by weight) is then removed via stream (5*b*). The aqueous formic acid in stream (5*b*) can optionally be returned to step (b) to remove the water.

The second variant plays a role as a rule when no secondary components or secondary components which do not adversely affect the desired formic acid quality and which boil lower than formic acid are present in the feed to the distillation apparatus C. In this case, the formic acid (for example having a formic acid content of up to 100% by weight) is then separated off via stream (5). Water-containing formic acid (for example having a formic acid content of from 75 to 95% by weight) is then as a rule removed via stream (5*a*). The aqueous formic acid in stream (5*a*) can optionally be returned to step (b) to remove the water. In this case, stream (5*b*) can usually be dispensed with.

The third variant plays a role as a rule when the desired formic acid quality is already achievable through the stream (5). This is the case, for example, when the content of water and secondary components boiling lower than formic acid in the feed to the distillation apparatus C is so low that the content thereof is in agreement with the desired quality requirements of the formic acid. This variant may therefore be important in particular for obtaining formic acid having a content of from 75 to 95% by weight.

In the column body C1, the feed of stream (4) is located in general between the side take-off of the streams (5*a*)/(5*b*) and the bottom of the column body C1 or, in a more preferred embodiment, in the region of the lower fourth of the available separation stages. The bottom product of the column body C1 is taken off as stream (6). Stream (6*a*) is fed to the bottom evaporator C2 for heating. Formic acid-containing vapor and optionally liquid stream comprising tertiary amine (I) and/or formic acid is recycled via stream (6*x*) to the column body C1. A part-stream (6*b*) of the bottom discharge is fed via an optional heat exchanger H, in which the stream is cooled, to the phase separation vessel D. The upper liquid phase is recycled as stream (8) to the apparatus A. The lower liquid phase is recycled as stream (7) to the distillation apparatus C.

Instead of the recycling of stream (7) to the bottom evaporator C2, stream (7) can also be recycled completely or partly into the bottom of the column body C1.

Figure 3:
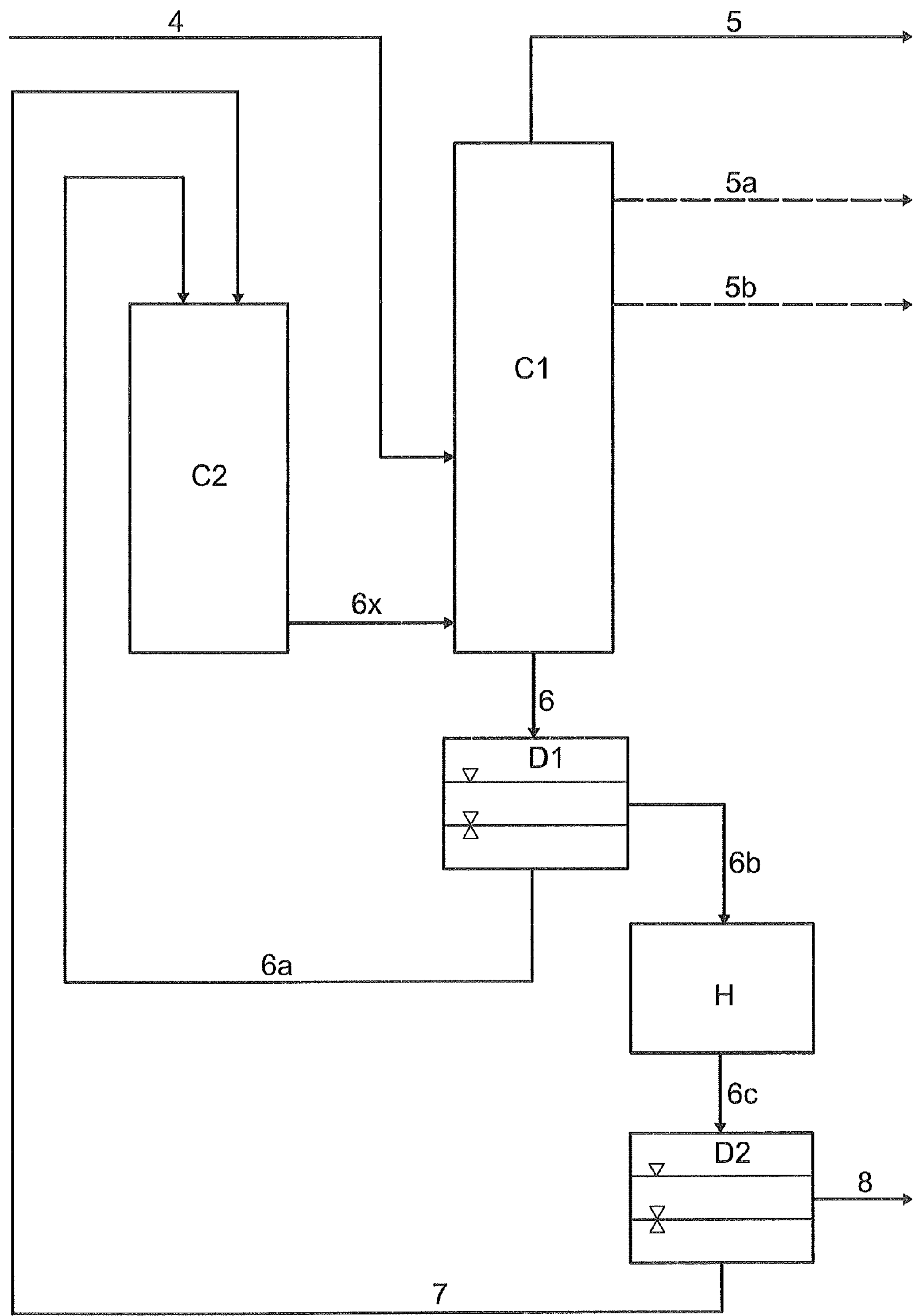
FIG. 3 shows a simplified block diagram of another configuration preferred in the process according to the invention, in the region of the distillation apparatus C and of the phase separation D.

FIG. 3 shows a simplified block diagram of another configuration preferred in the process according to the invention, in the region of the distillation apparatus C and of the phase separation D. There, the individual letters have the following meaning:

C1=Column body with internals

C2=Bottom evaporator

D1=Phase separation vessel in the evaporator circulation

D2=Phase separation vessel

H=Heat exchanger

Stream (4) comprising formic acid and tertiary amine (I) is fed to the column body C1. Depending on composition and origin of the feed comprising formic acid and a tertiary amine (I) to the distillation apparatus C, the formic acid is removed by distillation as top product via stream (5), as side product via stream (5*a*) and/or as side product via stream (5*b*), in particular the two variants mentioned in the description relating to FIG. 2 being followed. The feed of stream (4) to the column body C1 is located in general between the side take-off of the stream (5*a*) and the bottom of the column body C1 or, in a more preferred embodiment, in the region of the lower fourth of the available separation stages. The bottom product of the column body C1 is taken off as stream (6) and fed to the phase separation vessel in the evaporator circulation D1. The lower liquid phase is fed as stream (6*a*) to the bottom evaporator C2 for heating. Formic acid-containing vapor and optionally liquid stream comprising tertiary amine (I) and/or formic acid are fed via stream (6*x*) to the column body C1. The upper liquid phase of the phase separation vessel in the evaporator circulation D1 is fed as stream (6*b*), via an optional heat exchanger H in which the stream is cooled, to the phase separation vessel D2. The upper liquid phase is recycled as stream (8) to the apparatus A. The lower liquid phase is recycled as stream (7) to the distillation apparatus C.

In a simplified procedure, in the variant according to FIG. 3, the phase separation vessel D2, too, and optionally also the heat exchanger H can be dispensed with and the upper liquid phase can be removed as stream (6*b*) from the phase separation vessel in the evaporator circulation D1 and recycled as stream (8) to the apparatus A.

Instead of the recycling of stream (7) and/or stream (6*a*) to the bottom evaporator C2, stream (7) and/or stream (6*a*) can also be completely or partly recycled into the bottom of the column body C1.

Figure 4:
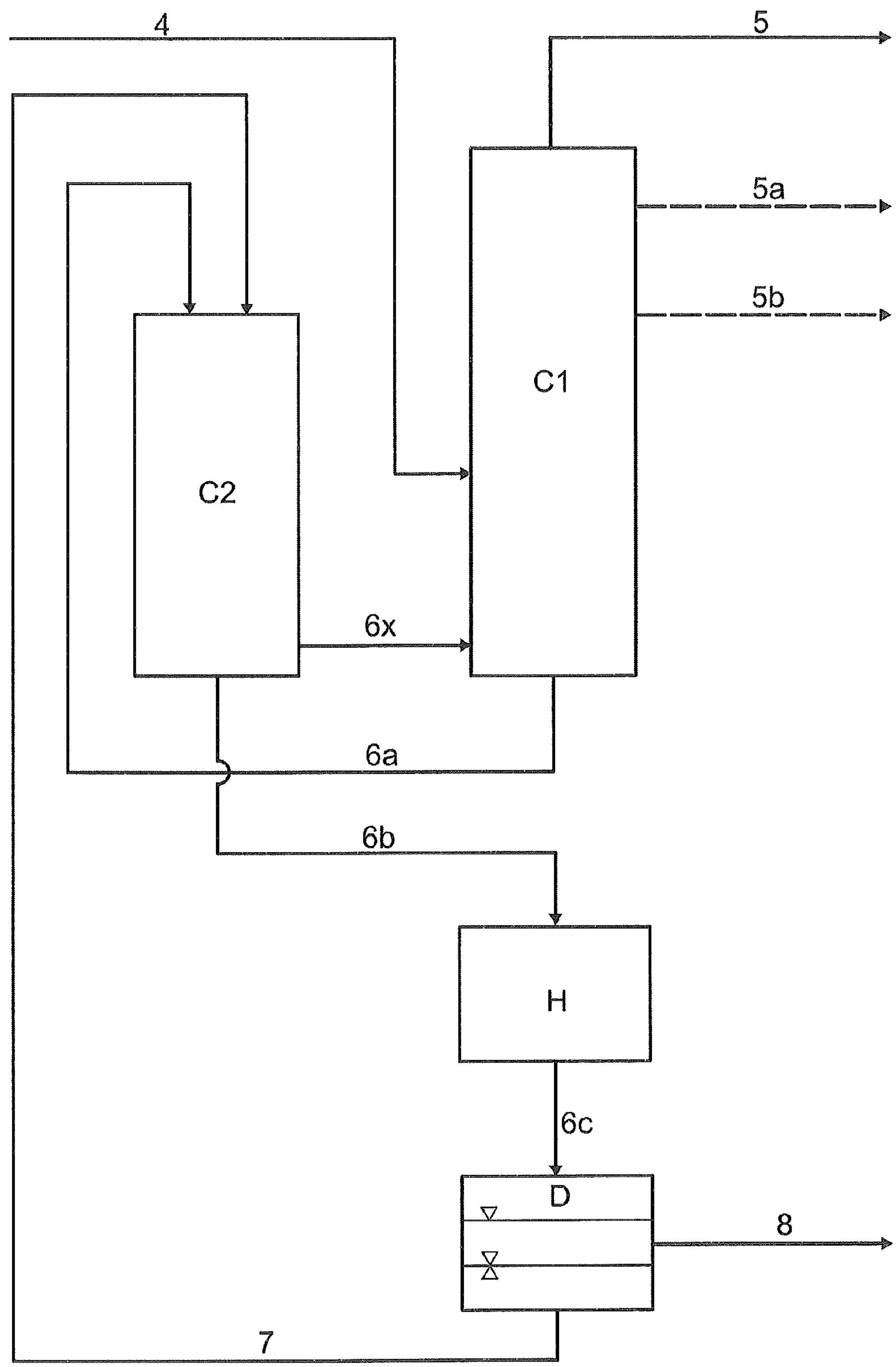
FIG. 4 shows a simplified block diagram of a further configuration preferred in the process according to the invention, in the region of the distillation apparatus C and the phase separation D.

FIG. 4 shows a simplified block diagram of a further configuration preferred in the process according to the invention, in the region of the distillation apparatus C and the phase separation D. There, the individual letters have the same meaning as in FIG. 2. The variant of FIG. 4 differs from that of FIG. 2 in that the feed of the phase separation vessel D, which optionally takes place via the heat exchanger H, originates not from the bottom of the column body C1 but from the bottom of the bottom evaporator C2. In this variant, too, stream (7) can also be completely or partly recycled into the bottom of the column body C1 instead of the recycling of stream (7) to the bottom evaporator C2.

Figure 5:
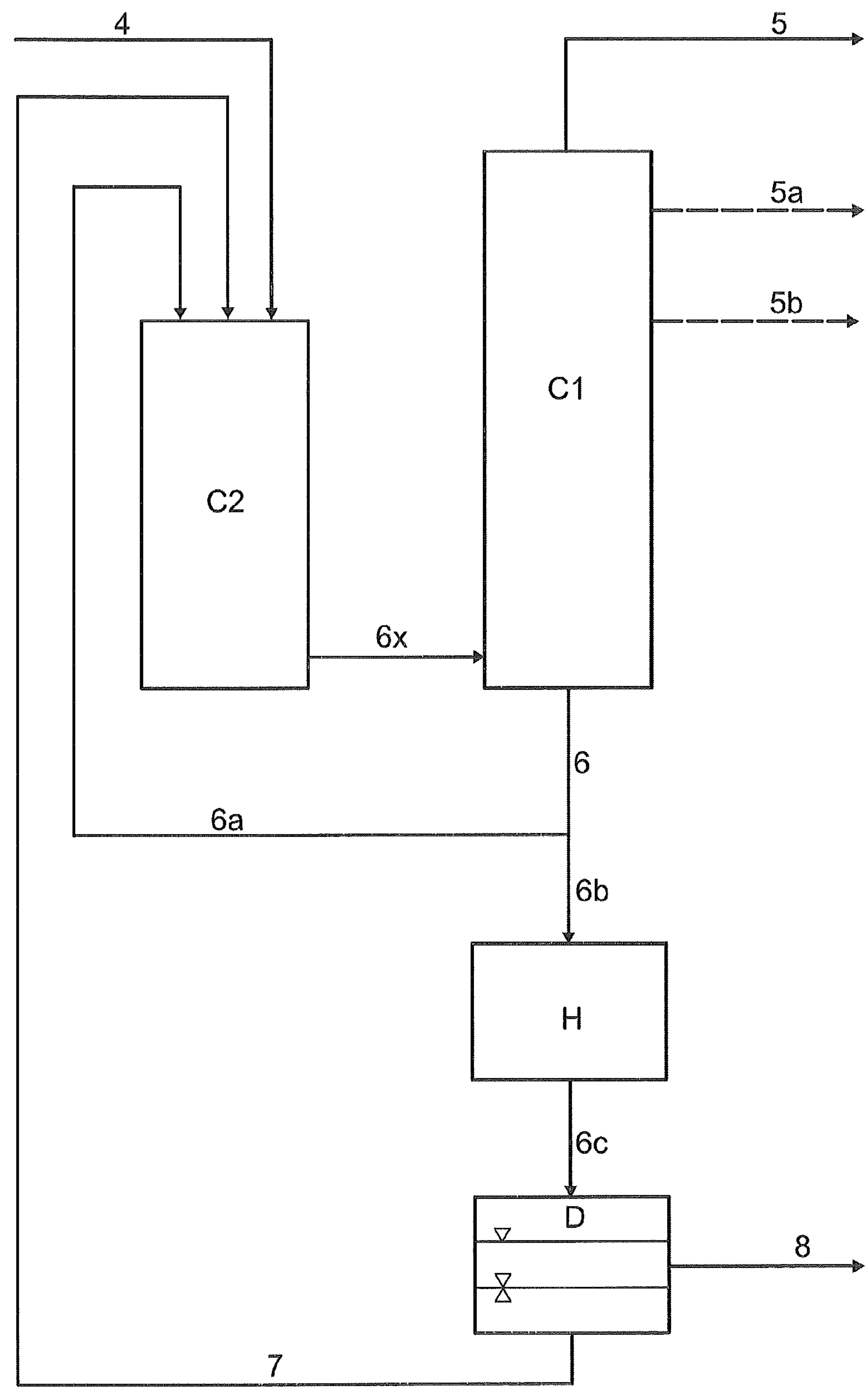
FIG. 5 shows a simplified block diagram of a further configuration preferred in the process according to the invention, in the region of the distillation apparatus C and of the phase separation D.

FIG. 5 shows a simplified block diagram of a further configuration preferred in the process according to the invention, in the region of the distillation apparatus C and of the phase separation D. There, the individual letters have the same meaning as in FIG. 2. The variant of FIG. 5 differs from that of FIG. 2 in that the stream (4) comprising formic acid and tertiary amine (I) is fed not to the column body C1 but to the bottom evaporator C2. In this variant, too, stream (7) can also be recycled completely or partly into the bottom of the column body C1 instead of the recycling of stream (7) to the bottom evaporator C2.

Figure 6:
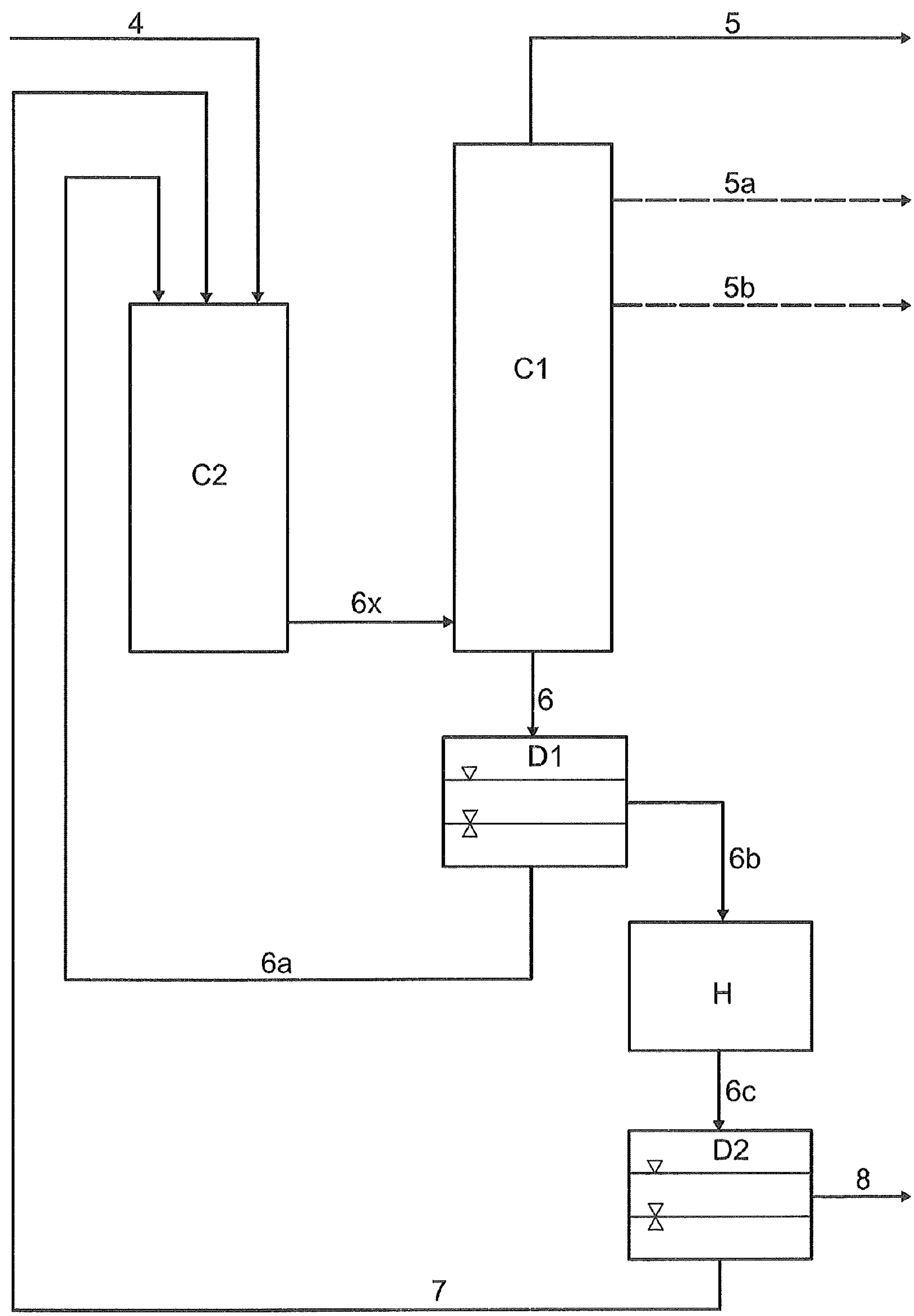
FIG. 6 shows a simplified block diagram of a further configuration preferred in the process according to the invention, in the region of the distillation apparatus C and of the phase separation D.

FIG. 6 shows a simplified block diagram of a further configuration preferred in the process according to the invention, in the region of the distillation apparatus C and of the phase separation D. There, the individual letters have the same meaning as in FIG. 3. The variant of FIG. 6 differs from that of FIG. 3 in that the stream (4) comprising formic acid and tertiary amine (I) is fed not to the column body C1 but to the bottom evaporator C2. In this variant, too, stream (7) and/or stream (6*a*) can also be recycled completely or partly into the bottom of the column body C1 instead of the recycling of stream (7) and/or stream (6*a*) to the bottom evaporator C2.

Figure 7:
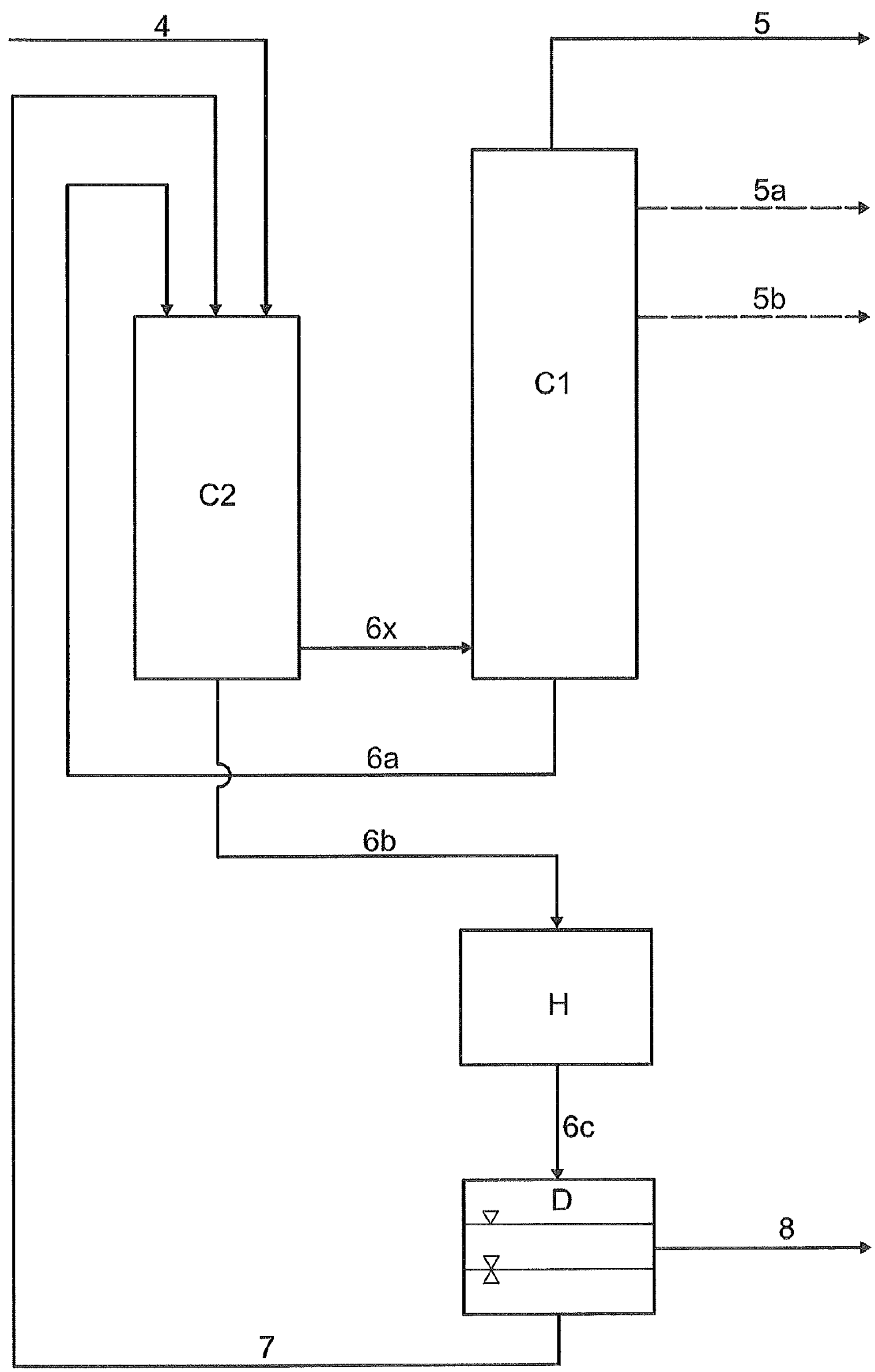
FIG. 7 shows a simplified block diagram of a further configuration preferred in the process according to the invention, in the region of the distillation apparatus C and of the phase separation D.

FIG. 7 shows a simplified block diagram of a further configuration preferred in the process according to the invention, in the region of the distillation apparatus C and of the phase separation D. There, the individual letters have the same meaning as in FIG. 2. The variant of FIG. 7 differs from that of FIG. 5 in that the feed of the phase separation vessel D, which optionally takes place via the heat exchanger H, originates not from the bottom of the column body C1 but from the bottom of the bottom evaporator C2. In this variant, too, stream (7) can also be recycled completely or partly into the bottom of the column body C1 instead of the recycling of stream (7) to the bottom evaporator C2.

Below, some specific embodiments for special fields of use of the process according to the invention are described.

Concentration of Formic Acid

A general embodiment for concentrating or purifying dilute and/or contaminated formic acid is based on the process described under FIGS. 1*a* and 1*b*. The formic acid source via stream (1) is the dilute and/or contaminated formic acid. In apparatus A, which may be, for example, a static mixer, a mixing nozzle, a stirred container, a reaction column (for example in the case of low-boiling impurities) or an extraction column (for example in the case of aqueous formic acid), stream (1) and the tertiary amine (I) from stream (8) are mixed with formation of a stream (2) comprising formic acid, tertiary amine (I) and diluting solvent (such as, for example, water) and/or contaminating secondary components (impurities). Via stream (2), the stream then enters apparatus B, in which the secondary components are partly or completely separated off.

In the case of low-boiling secondary components, these can also be separated off, for example, in apparatus A itself by the use of a so-called reaction column. In this case, the mixing of the formic acid source with the tertiary amine (I) would be effected, for example, in a reaction column or a reactor with attached distillation column, in which the low-boiling secondary components can be simultaneously removed by distillation.

If it is a matter of the concentration of water-diluted formic acid, the major part of the water can be separated off in apparatus B. If the water-diluted formic acid used is diluted to such an extent that stream (2) can be separated into two phases, a phase separation vessel is preferably used as apparatus B. The water phase settles out as the lower phase and can be removed. The upper phase comprises formic acid and tertiary amine (I) and is fed via stream (4) to the distillation apparatus C. The apparatuses A and B can in this case be combined into one apparatus, for example an extraction column, aqueous formic acid being fed in in the upper part of the column and the amine (I) in the lower part of the column. Water depleted in formic acid will then be taken off in the column bottom and the phase which comprises formic acid and amine (I) and may optionally still comprise small amounts of water will then be taken off at the top of the column. For improving the phase separation or for reducing the water content of the phase comprising amine (I) and formic acid, it is possible to add assistants, such as, for example, nonpolar hydrocarbons, such as, for example, octane or decane. Depending on the desired formic acid concentration of the product, it may be advantageous further to dewater the stream (4) comprising formic acid and tertiary amine (I), in an intermediate distillation column and only then to feed it to the distillation apparatus C.

The configuration in the region of the distillation apparatus C and the phase separation D can be effected, for example, as described in FIGS. 2 to 7. Secondary components which boil between formic acid and the tertiary amine (I) can be removed in the distillation apparatus C, for example also as a side stream. It may be appropriate to choose the tertiary amine (I) with regard to its boiling point so that a side take-off of the secondary components is possible. Any secondary components remaining in the bottom can, depending on the amount, be removed, for example, in a branched-off stream from the lower or upper liquid phase by suitable methods, such as, for example, evaporation, distillation or adsorption on active carbon.

By said concentration, for example, aqueous formic acid can be concentrated to 100% by weight.

Obtaining formic acid by hydrolysis of methyl formate

Figure 8:
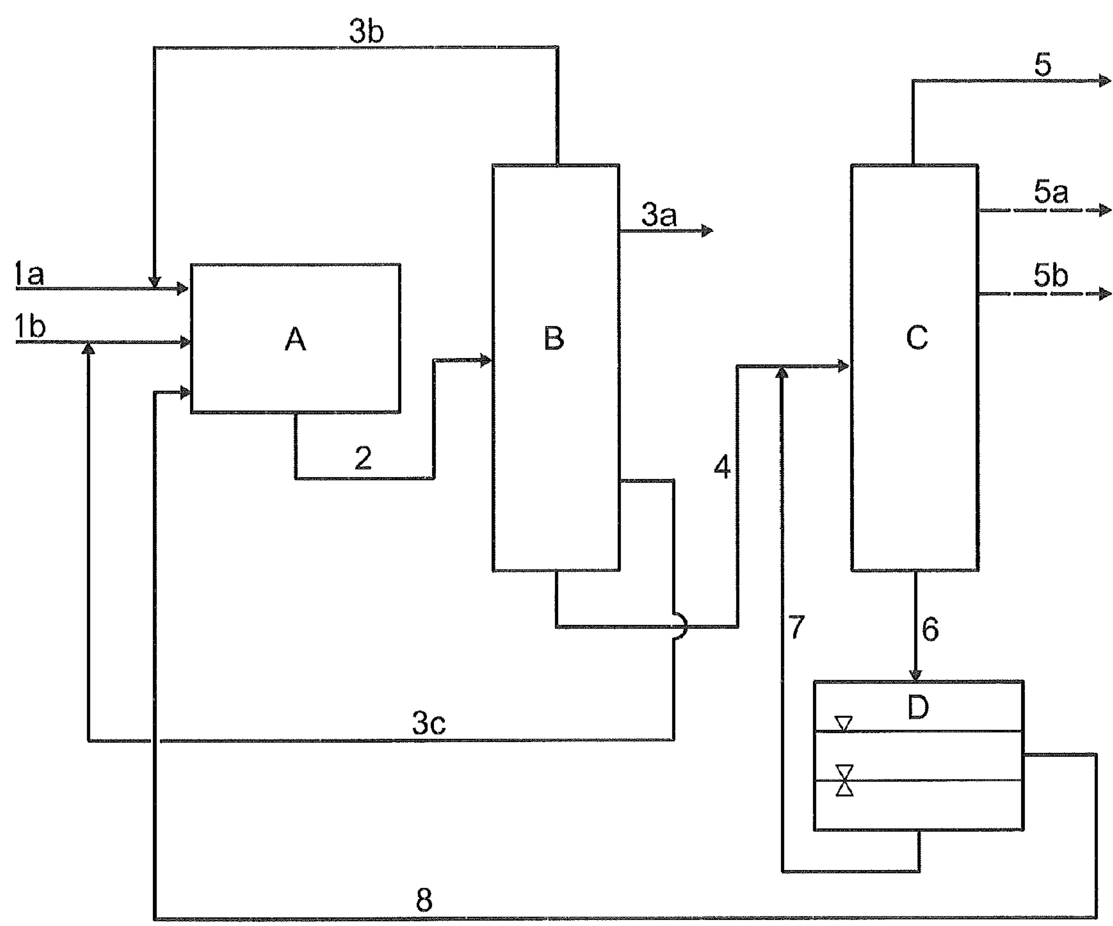
FIG. 8 shows a preferred embodiment for obtaining formic acid by hydrolysis of methyl formate is reproduced in by a simplified block diagram.

A preferred embodiment for obtaining formic acid by hydrolysis of methyl formate is reproduced in FIG. 8 by a simplified block diagram. There, the individual letters have the following meaning:

A=Apparatus for hydrolysis of methyl formate and production of a stream comprising formic acid and tertiary amine (I)

B=Distillation apparatus for separating off secondary components

C=Distillation apparatus for obtaining formic acid

D=Phase separation vessel

Methyl formate (streams (1*a*) and (3*b*)), water (streams (1*b*) and (3*c*)) and tertiary amine (I) (stream (8)) are fed to the apparatus A. In principle, all apparatuses in which a weakly exothermic reaction of fluid streams is possible can be used as apparatus A. Stirred tanks, tubular reactors or tube-bundle reactors, in each case without internals or with internals (such as, for example, beds, random packings, perforated metal sheets and the like) may be mentioned as examples. Apparatus A is preferably operated adiabatically or with cooling. Hydrolysis of methyl formate therefore results in a stream which comprises formic acid, tertiary amine (I), methanol, water and methyl formate and is removed as stream (2) from the apparatus A and fed to the apparatus B. The methyl formate conversion and hence the composition of the stream (2) depends primarily on the relative feed rates of the three feed streams methyl formate, water and tertiary amine (I) to the apparatus A, the type of tertiary amine (I) used, the residence time and the reaction temperature. The conditions which are expedient for the respective reaction system can easily be determined by the person skilled in the art, for example by preliminary experiments. Usually, the reaction takes place in a temperature range from 80 to 150° C. and a pressure range from 0.4 to 25 MPa abs. In stream (2), the molar ratio of formic acid to tertiary amine (I) is usually from 0.5 to 3, deviations from this range of course also being possible.

In the distillation apparatus B, so-called secondary components are now separated off from stream (2). These are primarily (i) unconverted methyl formate, which can be separated off as a low boiler via stream (3*b*), (ii) methanol which is formed in the hydrolysis and can likewise be separated off as a medium boiler via stream (3*a*), and (iii) unconverted water, which is separated off as a further medium boiler via stream (3*c*). The unconverted starting materials methyl formate and water which are separated off are recycled via stream (3*b*) and (3*c*), respectively, to the apparatus A. The methanol separated off via stream (3*a*) can be used again, for example, for the preparation of methyl formate. Formic acid and tertiary amine (I) are removed via stream (4). This also comprises residual amounts of water. Depending on the embodiment of the process, these may account for a few percent by weight or even a few ten percent by weight of the stream (4). Preferably, the water content in the stream (4) is 20% by weight, particularly preferably ≤10% by weight and very particularly preferably ≤5% by weight. The molar ratio of formic acid to tertiary amine (I) is not changed or only insignificantly changed by the distillation apparatus B, so that it is usually from 0.5 to 3 in stream (4) too, deviations from this range of course also being possible.

Stream (4) is fed to the distillation apparatus C. There, the formic acid is removed by distillation as top product via stream (5), as side product via stream (5*a*) and/or as side product via stream (5*b*). The explanation of FIG. 2 with regard to separating off formic acid via the streams (5), (5*a*) and/or (5*b*) also applies to the present embodiment. Depending on the framework conditions, i.e. especially the composition of the feed stream (4) to the distillation apparatus C and the desired purity of the formic acid, formic acid can be obtained in the present embodiment via the top as stream (5) or as side product as stream (5*a*). Water-containing formic acid is then removed as side product via stream (5*a*) or (5*b*). In the individual case, it may even be sufficient to remove formic acid or water-containing formic acid as top product only via stream (5). Depending on the specific embodiment, the side stream (5*b*) or even both side streams (5*a*) and (5*b*) can therefore be dispensed with. Regarding the possible embodiments of the distillation apparatus C, it may be noted that it can be designed, as described in FIG. 1*b*, also with an integrated phase separator. Furthermore, it may be noted that the configurations of FIGS. 2 to 7 are of course also preferred for the distillation apparatus C.

The bottom product of the distillation apparatus C is fed as stream (6) to the phase separation vessel D. As already mentioned above, this can of course also be integrated in the distillation apparatus C according to FIG. 1*b*. In the phase separation vessel D, the bottom product is separated into two liquid phases. As already mentioned in the case of the embodiments of FIGS. 2 to 7, a heat exchanger can optionally be connected between the distillation apparatus C and the phase separation apparatus D for cooling the bottom stream removed. Although a lower phase separation temperature leads as a rule to somewhat better separation with regard to the formic acid content, it gives rise to additional expense and energy consumption owing to the use of a heat exchanger. Advantages and disadvantages should therefore be considered in each case. The upper liquid phase from the phase separation vessel D is recycled via stream (8) to the apparatus A. The lower liquid phase is recycled via stream (7) to distillation apparatus C. Any secondary components remaining in the two recycle streams can, depending on amount, be removed, for example, in a branched-off stream from the lower or upper liquid phase by suitable methods, such as, for example, evaporation, distillation or adsorption on active carbon.

Figure 9:
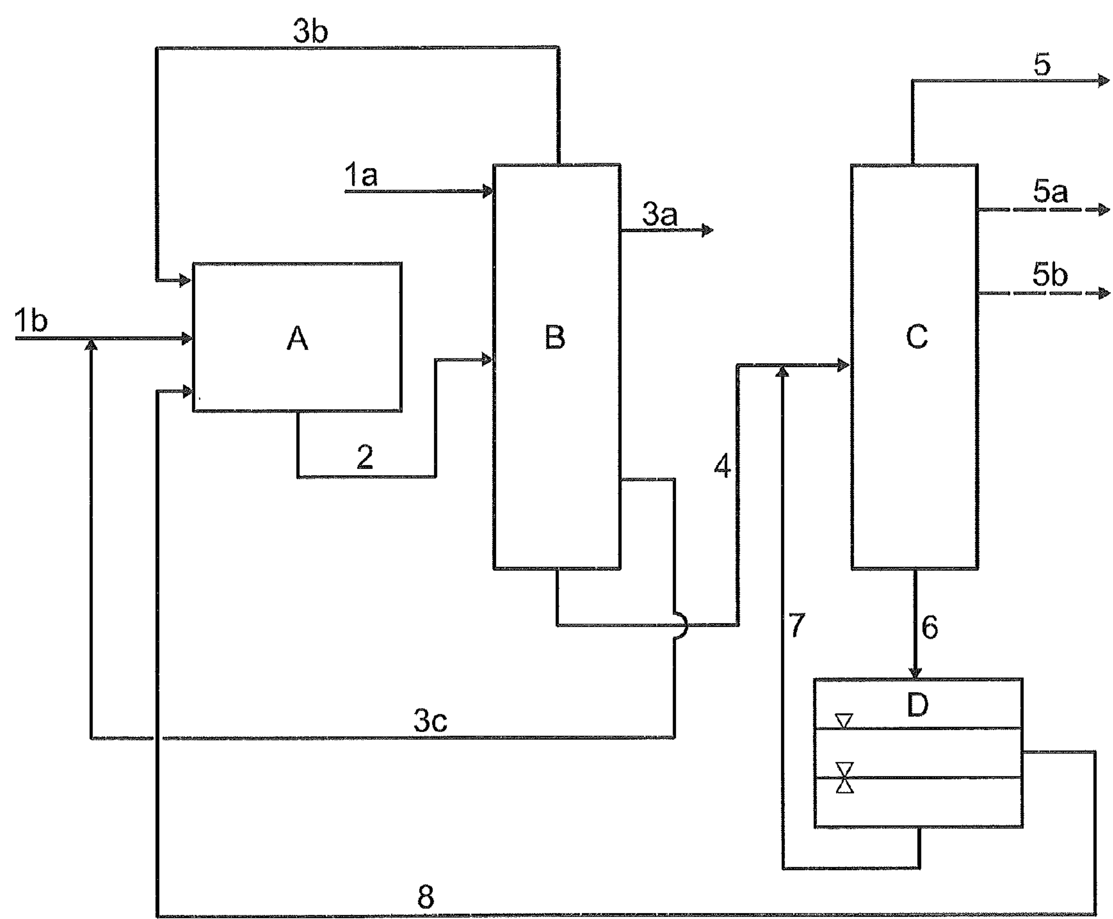
FIG. 9 shows another preferred embodiment for obtaining formic acid by hydrolysis of methyl formate, where the methyl formate stream (1*a*) is introduced into the distillation apparatus B.

In another, preferred embodiment for obtaining formic acid by hydrolysis of methyl formate, according to FIG. 9 the methyl formate stream (1*a*) is introduced into the distillation apparatus B. This embodiment is in general advantageous if the methyl formate available as stream (1*a*) is still contaminated with residual amounts of methanol, for example by a preceding methyl formate synthesis stage with partial methanol conversion and incomplete working-up of the methyl formate. By direct feeding of stream (1*a*) into the distillation apparatus B, the methanol present can therefore be separated off as stream (3*a*) and, for example, recycled to the methyl formate synthesis stage. By means of this variant, it is possible even completely to dispense with a methyl formate/methanol separation in the methyl formate synthesis stage and hence to save an entire distillation column and therefore also energy during operation.

Figure 10:
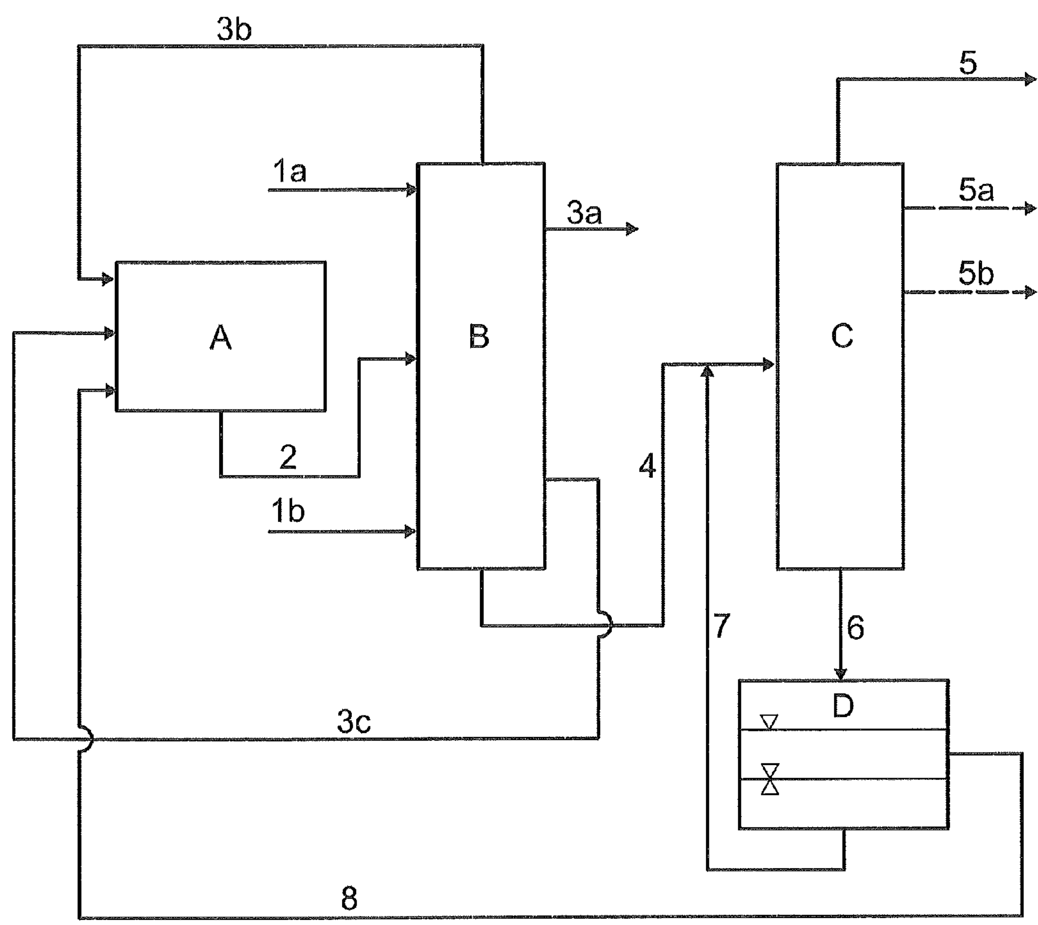
FIG. 10 shows another preferred embodiment for obtaining formic acid by hydrolysis of methyl formate, where both the methyl formate stream (1*a*) and the water stream (1*b*) are introduced into the distillation apparatus B.

In a further other, preferred embodiment for obtaining formic acid by hydrolysis of methyl formate, according to FIG. 10 both the methyl formate stream (1*a*) and the water stream (1*b*) are introduced into the distillation apparatus B. Regarding the water stream (1*b*), this embodiment is in general advantageous if hot condensate or steam is available as a water source since the thermal energy stored therein can thereby be used in the distillation apparatus B.

For completeness, it should also be mentioned that it is of course also possible, in a further embodiment, to introduce the methyl formate stream (1*a*) into the apparatus A and to introduce the water stream (1*b*) into the distillation apparatus B. This is advantageous, for example, if low-pressure excess steam is available.

In the variants of FIGS. 8 to 10, specific variants having one, two or even three distillation columns are possible with regard to the configuration of the distillation apparatus B. FIG. 11*a* shows a configuration having one distillation column. FIGS. 11*b* to 11*e* show different configurations having two distillation columns. FIGS. 12*a* to 12*c* show different configurations having three distillation columns. Variants having one or two distillation columns are preferred for configuring the distillation apparatus B. For the sake of completeness, it should be mentioned that, particularly in the case of the embodiments having one or two distillation columns, these may also be configured as a thermally coupled or dividing wall column.

The process according to the invention makes it possible to obtain formic acid in high yield and high purity by thermal separation of a stream comprising formic acid and a tertiary amine. The process can be carried out simply and reliably. The formic acid to be obtained has a low color number and a high color number stability.

The process according to the invention also ensures that only extremely small amounts of formic acid or even virtually no formic acid are or is transported back to the formic acid source in the amine-containing recycled stream from the process step of the distillative separation of the formic acid. Larger amounts of formic acid in the recycled stream would lead to increased process streams and may therefore result in both higher capital costs and higher energy consumptions. This has an effect particularly in the case of hydrolysis of methyl formate, in which recycled formic acid would lead to a decrease in the methyl formate conversion. Thus, in the process without phase separation, it is therefore necessary to work permanently with high separation rates when separating off the formic acid by distillation, in order to achieve a low formic acid concentration in the recycled amine stream. Any faults occurring during operation of the distillation apparatus which lead to a lower separation rate are therefore propagated directly to the downstream process steps. In the worst case, stable operation of the plant would no longer be possible and the plant would have to be operated with reduced capacity or, if necessary, even shut down. This would mean a partial or even complete loss of production. In contrast, in the process according to the invention, high variability of the separation rate is achieved by the phase separation downstream of the distillative separation of the formic acid in process step (c) and recycling of the upper liquid phase of the phase separation to step (a). In step (c), formic acid which has not been separated off is present in the lower liquid phase of the phase separation. The operation of the process stage for the distillative separation of the formic acid can therefore easily be adapted to the requirements of an optimized overall process and varied. The process according to the invention is therefore also less susceptible to operational faults.

Owing to the milder conditions in the thermal separation with regard to the temperature program, the corrosion rate and the distillation apparatus is furthermore lower than in the processes according to the prior art, in which a substantially lower content of formic acid is strived for in the bottom. Thus, as a rule, a decrease in the corrosion rate by a factor of from 2 to 3 is to be expected at a temperature which is 10° C. lower. This has positive effects firstly on the stability of the column material but secondly also on the content of undesired traces of foreign metals in the bottom, which is lower in the process according to the invention than in a corresponding process according to the prior art. Regarding the traces of foreign metals, there is even a further advantage in addition to the lower concentration. This is based on the fact that the corrosion metals are present virtually exclusively in the polar, lower liquid phase and therefore the upper liquid phase predominantly comprising the tertiary amine (I) is in principle free of foreign metals. The dissolved foreign metals can be discharged in a targeted manner via the lower liquid phase, optionally via a purge stream or at least localized via the recycled stream in step (f). The foreign metals are therefore also not recycled or are recycled only to the smallest extent to the formic acid source (i.e. the process step (a)) and they therefore cannot have any adverse effects there and in the subsequent process steps. In contrast, in the processes according to the prior art, the foreign metals are recycled with the single-phase bottom product comprising the tertiary amine (I) into the process step (a) and lead there and in the downstream plant parts to deposits in the plant in the course of time. These would adversely affect the operability in the course of time.

Furthermore, owing to the milder conditions in the thermal separation, the process according to the invention also has the advantage that the distillation apparatus can be operated at lower temperature. Thus, it is also possible, for example, to use low-energy steam for operating the distillation apparatus.

Furthermore, the milder conditions lead to a smaller loss of formic acid due to thermal decomposition.

The process according to the invention can also be used in particular in combination with the hydrolysis of methyl formate as a formic acid source and has technical and economic advantages over the production processes currently practiced industrially and involving methyl formate hydrolysis with downstream dewatering by means of an extraction assistant or a two-pressure distillation.

EXAMPLES

Examples 1 to 10

One mole of the desired tertiary amine was initially taken in a glass flask stirred by means of a magnetic stirrer and one mole of formic acid (98-100% by weight) was added dropwise per mole of amine nitrogen while cooling in an ice bath. After the end of the addition, the solution was warmed up to room temperature (about 20° C.) and stirred for 30 minutes to ensure that the two phases were present in equilibrium. Thereafter, the phases were separated by means of a separating funnel and weighed. In each phase, the formic acid content was determined by titration with 0.1 N NaOH in isopropanol (end point determination:potentiometric). The amine content was assumed as the remainder to 100%. The molar ratio of formic acid to amine was then calculated from the composition. The individual experimental data are shown in Table 1. Examples 1 to 10 show that a broad selection of tertiary amines form two-phase mixtures with formic acid.

Comparative Examples 11 and 14 and Examples 12 and 13

Examples 11 to 14 were carried out analogously to Example 3, but with the difference that the added amount of formic acid (expressed as overall molar formic acid/amine ratio) was varied. The results are shown in Table 2.

These show that, for example, the two-phase character of a system may also be dependent on the molar formic acid/amine ratio.

Comparative Example 15 and Examples 16 to 17

In Comparative Example 15, one mole of methyldicyclohexylamine was initially taken in a glass flask stirred by means of a magnetic stirrer and 0.21 mol of formic acid (98-100% by weight) was added dropwise at room temperature. After the end of the addition, the solution was stirred for 30 minutes. The product obtained was solid (cf. Table 3).

In Examples 16 to 17, one mole of methyldicyclohexylamine was likewise initially taken in a glass flask stirred by means of a magnetic stirrer and 0.21 mol of formic acid (98-100% by weight) was added at room temperature. Thereafter, however, stirring was effected for 10 minutes at room temperature and 0.5 g of solvent was then added dropwise per gram of amine used. After the end of the addition, stirring was effected for 30 minutes. Thereafter, the phases were separated by means of a separating funnel and weighed. The content of formic acid in each phase was determined by titration with 0.1 N KOH in methanol against bromo-thymol blue, and the content of tertiary amine and diol was determined in both phases by gas chromatography in each case. The results are shown in Table 3.

The examples show that, for example in the absence of a phase separation (as, for example, in Comparative Example 15) by addition of a suitable polar solvent, separation into two liquid phases can be induced, the formic acid being present in higher concentration together with the polar solvent in the lower phase.

Comparative Example 18 and Examples 19 to 21

These examples were carried out as in Examples 15 to 17, but one mole of dimethyl-n-dodecylamine and 0.23 mol of formic acid were used. The results are shown in Table 4. Here too, it is found that separation into two liquid phases can be induced by addition of a suitable polar solvent.

Comparative Example 22 and Examples 23 to 24

These examples were carried out as in Examples 15 to 17, but one mole of dimethyl-n-tetradecylamine and 0.26 mol of formic acid were used. The results are shown in Table 5. In the formic acid/dimethyl-n-tetradecylamine system, too, the addition of a suitable polar solvent induces a separation into two liquid phases.

Laboratory Plant 1

Laboratory plant 1 served for examination of steps (c) and (d) of the process according to the invention. The simplified block diagram of laboratory plant 1 is shown in FIG. 13. The individual letters therein have the following meanings:

- C1=column body (internal diameter 32 mm) with 18 bubble-cap trays and condenser, and controllable reflux divider at the top of the column
- C2=bottom evaporator (oil-heated thin-film evaporator having a surface area of 0.046 $m^2$ and a wiper blade speed of 500 $min^{-1}$)
- D=separate phase separation vessel (oil-heated, total volume 0.3 l)

The apparatuses of laboratory plant 1 consisted of glass, and the connecting lines of Teflon. Laboratory plant 1 was operated continuously under reduced pressure.

In all experiments in laboratory plant 1, the content of formic acid in each case was determined by potentiometric titration with 0.5 N NaOH in water, and the content of water according to Karl Fischer. All other organic components were determined by gas chromatography in each case.

Laboratory plant 1 relates to the essential process parts of the distillative separation of formic acid and of the phase separation for enabling the separate recycling of the upper and lower liquid phases, and is a model, inter alia, also for the concentration and purification of formic acid which has, for example, been obtained beforehand by the hydrolysis of methyl formate.

Example 25

Example 25 was carried out in laboratory plant 1. The distillation apparatus was operated at a top pressure in column body C1 of 0.01 MPa abs and a reflux ratio of reflux to distillate of 4. Via stream (4), 585 g/h of a mixture of tri-n-octylamine and formic acid (molar ratio of formic acid: amine=1.3) were fed into the top of the thin-film evaporator C2. The temperature at the lower outlet of the thin-film evaporator was 143° C. The gaseous discharge of the evaporator was fed to the column body C1 as stream (6*x*). The liquid output of the column body was fed into the top of the thin-film evaporator C2 as stream (6*a*). The top product obtained from the column body C1, as stream (5), was 45.5 g/h of 99% by weight formic acid. This formic acid comprised only 13 ppm by weight of organic impurities and had an APHA color number of 1, which remained unchanged even after 9 days of storage at room temperature.

The liquid discharge of the thin-film evaporator was passed as stream (6*b*) to the phase separation vessel D. This was operated at a temperature of 30° C. The upper liquid phase was taken off continuously as stream (8) at 367 g/h. Stream (8) comprised 98.5% by weight of tri-n-octylamine and only 1.4% by weight of formic acid, which corresponds to a molar ratio of formic acid:amine of 0.1. The lower liquid phase was taken off continuously as stream (7) at 164 g/h. Stream (7) comprised 86% by weight of tri-n-octylamine and 14% by weight of formic acid, which corresponds to a molar ratio of formic acid:amine of 1.25. In total, there was a ratio of formic acid:amine=0.43 in stream (6*b*).

The formic acid loss as a result of decomposition was determined by measuring offgas rate and offgas composition via the proportions of the hydrogen, carbon dioxide and carbon monoxide decomposition products determined by gas chromatography. Only 0.3% formic acid was decomposed, based on the formic acid obtained as distillate.

Example 25 shows the inventive obtaining of very pure and color number-stable formic acid while simultaneously obtaining two liquid phases from the bottom output of the distillation apparatus, the upper liquid phase consisting almost completely of tri-n-octylamine and thus being very suitable for recycling to step (a), and the lower liquid phase comprising 14% by weight of formic acid and 86% by weight of tri-n-octylamine being very suitable for recycling to step (b) and/or (c).

Example 26

Example 26 was carried out like Example 25, except that the stream (7) collected from Example 25 was used as stream (4) instead of a synthetic mixture of tri-n-octylamine and formic acid. The product obtained as stream (5) as the top product of the column body C2 comprised 22 ppm by weight of organic by-products and had an APHA color number of 2. The formic acid loss as a result of decomposition remained very low at 0.3%, based on the formic acid obtained as distillate.

Example 26 confirms that the lower liquid phase from step (d) can be recycled via stream (7) to step (c) without any problem and without evident losses in the quality of the formic acid obtained by distillation.

Example 27

Example 27 was likewise carried out in laboratory plant 1. The distillation apparatus was operated at a top pressure in column body C1 of 0.015 MPa abs and a reflux ratio of reflux to distillate of 4. Via stream (4), 533 g/h of a mixture of tri-n-hexylamine and formic acid (molar ratio of formic acid: amine=1.5) were fed into the top of the thin-film evaporator C2. The temperature at the lower outlet of the thin-film evaporator was 158° C. The gaseous discharge of the evaporator was fed to the column body C1 as stream (6*x*). The liquid output of the column body was fed into the top of the thin-film evaporator C2 as stream (6*a*). The top product obtained from the column body C1, as stream (5), was 78 g/h of 99% by weight formic acid. This formic acid comprised only 25 ppm by weight of organic impurities and had an APHA color number of 5, which remained unchanged even after 49 days of storage at room temperature.

The liquid discharge of the thin-film evaporator was passed as stream (6*b*) to the phase separation vessel D. This was operated at a temperature of 80° C. The upper liquid phase was taken off continuously as stream (8) at 364 g/h. Stream (8) comprised 99.0% by weight of tri-n-hexylamine and only 1.0% by weight of formic acid, which corresponds to a molar ratio of formic acid:amine of 0.06. The lower liquid phase was taken off continuously as stream (7) at 73 g/h. Stream (7) comprised 78% by weight of tri-n-hexylamine and 20% by weight of formic acid, which corresponds to a molar ratio of formic acid:amine of 1.5. In total, there was a ratio of formic acid:amine=0.26 in stream (6*b*).

The formic acid loss as a result of decomposition was determined by measuring offgas rate and offgas composition via the proportions of the hydrogen, carbon dioxide and carbon monoxide decomposition products determined by gas chromatography. Only 0.2% formic acid was decomposed, based on the formic acid obtained as distillate.

Example 27 shows that, even in the case of variation of the process conditions and especially also in the case of use of a different tertiary amine than in Example 25, a very pure and color-stable formic acid can be obtained by the process according to the invention. In this case too, two liquid phases were obtained from the bottom output of the distillation apparatus, and the upper liquid phase consisted virtually completely of tri-n-hexylamine and is therefore very suitable for recycling to step (a), and the lower liquid phase comprising 20% by weight of formic acid and 78% by weight of tri-n-hexylamine is very suitable for recycling to step (b) and/or (c).

Example 28

Example 28 was carried out essentially like Example 27, except that the stream (7) collected from Example 27 was used as stream (4) instead of a synthetic mixture of tri-n-hexylamine and formic acid. Via stream (4), 518 g/h of this mixture were fed into the top of the thin-film evaporator C2. The temperature at the lower outlet of the thin-film evaporator was 160° C. The top product obtained from the column body C1 as stream (5) was 76 g/h of 99% by weight formic acid. This formic acid comprised only 31 ppm by weight of organic impurities and had a APHA color number of 3.

The liquid output of the thin-film evaporator was passed as stream (6*b*) to the phase separation vessel D. This was operated at a temperature of 80° C. The upper liquid phase was taken off continuously as stream (8) at 407 g/h. Stream (8) comprised 98.0% by weight of tri-n-hexylamine and only 1.4% by weight of formic acid, which corresponds to a molar ratio of formic acid:amine of 0.08. The lower liquid phase was taken off continuously as stream (7) at 7 g/h. Stream (7) comprised 79% by weight of tri-n-hexylamine and 19% by weight of formic acid, which corresponds to a molar ratio of formic acid:amine of 1.4. In total, a ratio of formic acid: amine=0.1 was present in stream (6*b*). The formic acid loss as a result of decomposition was 0.7%, based on the formic acid obtained as distillate.

Example 28 confirms that, even in the case of use of a different tertiary amine than in Example 26, the lower liquid phase from step (d) can be recycled via stream (7) to step (c) without any problem and without evident losses in the quality of the formic acid obtained by distillation.

Comparative Example 29

Comparative Example 29 was likewise carried out in laboratory plant 1. The distillation apparatus was operated at a top pressure in the column body C1 of 0.015 MPa abs and a reflux ratio of reflux to distillate of 4. Via stream (4), 492 g/h of a mixture of tri-n-hexylamine and formic acid (molar ratio of formic acid:amine=1.5) were fed into the top of the thin-film evaporator C2. The temperature at the lower outlet of the thin-film evaporator was 171° C. The gaseous discharge of the evaporator was fed as stream (6*x*) to the column body C1. The liquid output of the column body was fed as stream (6*a*) into the top of the thin-film evaporator C2. As the top product of the column body C1, 72 g/h of 99% by weight formic acid were obtained as stream (5). This formic acid had an APHA color number of 10 which, however, had risen to 20 after only 7 days of storage at room temperature.

The liquid discharge of the thin-film evaporator was passed as stream (6*b*) to the phase separation vessel D which was operated at a temperature of 80° C. However, only a monophasic liquid discharge was obtained. This comprised 99.2% by weight of tri-n-hexylamine and 0.7% by weight of formic acid. The formic acid loss as a result of decomposition was again determined by measuring offgas rate and offgas composition via the proportions of the hydrogen, carbon dioxide and carbon monoxide decomposition products determined by gas chromatography. A very high decomposition value of 1.9% formic acid was determined here, based on the formic acid obtained as distillate.

Comparative Example 29 shows that an increased decomposition of formic acid took place when a monophasic liquid discharge was obtained from the distillation apparatus.

Example 30

In Example 30, the laboratory plant 1 was operated as in Example 27, but with the difference that, in the bottom of the column body C1 and in the bottom of the thin-film evaporator C2, a stainless steel plate (20 mm×50 mm×3 mm) made from the material with material numbers 1.4406, 1.4462 and 1.4439 was mounted in each case. The plant was subsequently operated continuously for 15 days, and, as a further difference from Example 27, the two liquid streams (7) and (8) were combined again and mixed with fresh anhydrous formic acid so as to establish a constant ratio of formic acid: tri-n-hexylamine of 1.5. This mixture was used as feed stream (4).

After 15 days, the content of the corrosion metals Cr, Fe, Mo and Ni in streams (7) and (8) was determined quantitatively by ICP-MS (inductively coupled plasma mass spectrometry). In the upper liquid phase (stream (8)), the content of all corrosion metals was below the detection limit of 1 ppm by weight. The lower liquid phase (stream (7)) comprised 32 ppm by weight of Cr, 42 ppm by weight of Fe, 7 ppm by weight of Mo and 2 ppm by weight of Ni.

Example 30 shows that the corrosion metals are present specifically in the lower liquid phase and can therefore be discharged therefrom, even in a controlled manner, by suitable measures. The upper liquid phase to be recycled to step (a) is actually free of corrosion metals.

Laboratory Plant 2

Laboratory plant 2 served for examination of step (b) of the process according to the invention, or specifically for examination of the dewatering of a mixture comprising formic acid, tertiary amine (I) and water. Laboratory plant 2 comprised a continuously operated distillation column made from glass (internal diameter=32 mm) with 20 bubble-cap trays. The heat was introduced via an oil-heated bottom (jacket). At the top of the column were a condenser and a reflux divider, by means of which the reflux ratio could be established. The column feed was fed into the column at the ninth bubble-cap tray (counted from the bottom). The column was operated at ambient pressure with a reflux ratio of in each case 0.5.

Example 31

Example 31 was carried out in laboratory plant 2. 230 g/h of a mixture comprising 8.0% by weight of water, 30.5% by weight of formic acid and 61.5% by weight of tri-n-hexylamine were fed into the column, which corresponds to a molar ratio of formic acid:amine of 2.9 and a mass ratio of formic acid:water of 79:21. In the steady state, a bottom temperature of 155° C. was established. The distillate comprised essentially water with only 0.16% by weight of formic acid. The bottom product comprised 32.7% by weight of formic acid, 65.8% by weight of tri-n-hexylamine and only 1.5% by weight of water, corresponding to a molar ratio of formic acid:amine of 2.9 and a mass ratio of formic acid: water of 96:4. Thus, 81% of the secondary component water was separated off.

Example 32

Example 32 was carried out like Example 31, but with the difference that 262 g/h of a mixture comprising 8.2% by weight of water, 40.6% by weight of formic acid and 51.3% by weight of tri-n-hexylamine were fed into the column, which corresponds to a molar ratio of formic acid:amine of 4.6 and a mass ratio of formic acid:water of 83:17. In the steady state, a bottom temperature of 137° C. was established. The distillate comprised essentially water with only 0.05% by weight of formic acid. The bottom product comprised 43.4% by weight of formic acid, 54.7% by weight of tri-n-hexylamine and only 1.9% by weight of water, corresponding to a molar ratio of formic acid:amine of 4.6 and a mass ratio of formic acid:water of 96:4. Thus, 77% of the secondary component water was separated off.

Examples 31 and 32 show that even a relatively simple distillation can without any problem separate about 80% of the water present from an aqueous mixture of formic acid and tri-n-hexylamine.

Laboratory Plant 3

Laboratory plant 3 served for examination of steps (a) and (b) of the process according to the invention, more specifically for examination of the hydrolysis of methyl formate and of the subsequent distillative removal of unconverted methyl formate, methanol formed and water. The simplified block diagram of the laboratory plant 3 is shown in FIG. 14. The individual letters therein have the following meanings:

A1=stirred tank (volume 3.5 l, electrically heated)

A2=tubular reactor (internal diameter 80 mm, length 1200 mm, filled with 2 mm glass beads, electrically heated)

B1=distillation apparatus with column body (internal diameter 55 mm, equipped with fabric packings each of packing height 1.3 m and of specific surface area 750 $m^2/m^3$, the feed being between the two packing beds) and oil-heated falling-film evaporator (surface area 0.45 $m^2$)

B2=distillation apparatus with column body (internal diameter 55 mm, equipped with fabric packings each of packing height 1.3 m and of specific surface area 750 $m^2/m^3$, the feed being between the two packing beds) and oil-heated falling-film evaporator (surface area 0.15 $m^2$)

The apparatuses and lines of the laboratory plant 3 consisted of a nickel-base alloy with material number 2.4610. To measure the mass flows, coriolis flow meters were used. Laboratory plant 3 was operated continuously.

Example 33

Example 33 was carried out in laboratory plant 3. Via metering pumps, 853 g/h of methyl formate were metered into the reactor A1 via stream (1*a*), 256 g/h of water via stream (1*b*), and 1535 g/h of tri-n-hexylamine via stream (8). Reactor A1 was operated at 130° C. and pressure 1.2 MPa gauge. The discharge of reactor A1 was passed into the postreactor A2, which was likewise operated at 130° C. and pressure 1.2 MPa gauge. The stream (2) obtained was a product mixture comprising 58.1% by weight of tri-n-hexylamine, 15.0% by weight of formic acid, 10.4% by weight of methanol, 3.8% by weight of water and 12.7% by weight of methyl formate, which corresponds to a molar ratio of formic acid: amine of 1.51. Stream (2) was decompressed and passed into the column body of the distillation apparatus B1. At a top pressure of 0.18 MPa abs and a reflux ratio of 1.7, the top product taken off as stream (3*b*) was a mixture which comprises essentially methanol formed and unconverted methyl formate. The bottom product obtained as stream (3*d*) was 1990 g/h of a mixture of 74.9% by weight of tri-n-hexylamine, 5.3% by weight of water, 19.8% by weight of formic acid and 0.1% by weight of methanol. The bottom temperature in the column body was 133° C. Stream (3*d*) was decompressed and passed into the column body of the distillation apparatus B2. Via stream (5*a*), 69 g/h of aqueous formic acid (formic acid content 82.5% by weight) were additionally supplied to the column body in order to simulate recycling of aqueous formic acid as can be obtained as a side take-off of the distillation apparatus in step (c) and recycled to step (b) according to the description for FIG. 2. As the top product of the distillation apparatus B2, 92 g/h were taken off at a top pressure of 0.11 MPa abs and a reflux ratio of 1.7, which comprised essentially water and 0.1% formic acid. Via stream (4), the bottom product obtained at a bottom temperature in the column body of 160° C. was 1949 g/h of a mixture of 76.9% by weight of tri-n-hexylamine, 21.2% by weight of formic acid and 1.9% by weight of water. The molar ratio of formic acid:amine in stream (4) was 1.61.

Example 33 shows that the process according to the invention, also in the case of hydrolysis of methyl formate and the subsequent workup thereof by removal of secondary components, especially of residual methyl formate, methanol formed and water, a stream greatly enriched in formic acid and tri-n-hexylamine can be obtained. This stream can then, as shown indirectly by Examples 27 and 28, be used for distillative separation of very pure formic acid.

TABLE 1

| Example | Amine | Molar formic acid/amine ratio in upper phase | Molar formic acid/amine ratio in lower phase |
|---|---|---|---|
| 1 | Tri-n-butylamine | 0.023 | 1.7 |
| 2 | Tri-n-pentylamine | 0.018 | 1.8 |
| 3 | Tri-n-hexylamine | 0.056 | 1.6 |
| 4 | Tri-n-octylamine | 0.085 | 1.4 |
| 5 | Triisopentylamine | 0.069 | 1.6 |
| 6 | Tri(2-ethylhexyl)amine | 0.009 | 3.3 |
| 7 | Methyl-di-n-octylamine | 0.090 | 1.2 |
| 8 | Methyldi(2-ethylhexyl)amine | 0.043 | 2.0 |
| 9 | N,N,N,N-Tetramethyl-1,6-hexanediamine | 0.026 | 1.1 |
| 10 | N-Ethylpiperidine | 0.020 | 1.3 |

TABLE 2

| Example | Amine | Molar formic acid/amine ratio overall | Molar formic acid/amine ratio in upper phase | Molar formic acid/amine ratio in lower phase |
|---|---|---|---|---|
| 11 | Tri-n-hexylamine | 0.03 | Single-phase mixture | |
| 12 | Tri-n-hexylamine | 0.6 | 0.056 | 1.6 |
| 13 | Tri-n-hexylamine | 1.2 | 0.056 | 1.6 |
| 14 | Tri-n-hexylamine | 1.8 | Single-phase mixture | |

TABLE 3

| Example | Amine | Solvent | Molar formic acid/amine ratio overall | Molar formic acid/amine ratio in upper phase | Molar formic acid/amine ratio in lower phase |
|---|---|---|---|---|---|
| 15 | Methyldicyclohexylamine | — | 0.21 | Solid formation at room temperature | |
| 16 | Methyldicyclohexylamine | Ethylene glycol | 0.21 | 0.001 | 0.98 |
| 17 | Methyldicyclohexylamine | 2-Methyl-1,3-propanediol | 0.21 | 0.001 | 0.81 |

TABLE 4

| Example | Amine | Solvent | Molar formic acid/amine ratio overall | Molar formic acid/amine ratio in upper phase | Molar formic acid/amine ratio in lower phase |
|---|---|---|---|---|---|
| 18 | Dimethyl-n-dodecylamine | — | 0.23 | Single-phase mixture | |
| 19 | Dimethyl-n-dodecylamine | Ethylene glycol | 0.23 | 0.004 | 0.49 |
| 20 | Dimethyl-n-dodecylamine | 1,4-Butanediol | 0.23 | 0.007 | 0.63 |
| 21 | Dimethyl-n-dodecylamine | 1,3-Propanediol | 0.23 | 0.001 | 0.57 |

TABLE 5

| Example | Amine | Solvent | Molar formic acid/amine ratio overall | Molar formic acid/amine ratio in upper phase | Molar formic acid/amine ratio in lower phase |
|---|---|---|---|---|---|
| 22 | Dimethyl-n-tetradecylamine | — | 0.26 | Single-phase mixture | |
| 23 | Dimethyl-n-tetradecylamine | Ethylene glycol | 0.26 | 0.004 | 0.42 |
| 24 | Dimethyl-n-tetradecylamine | 1,4-Butanediol | 0.26 | 0.001 | 0.52 |

The invention claimed is:

1. A process for obtaining formic acid by thermal separation of a stream comprising formic acid and a tertiary amine (I), comprising (a) producing a liquid stream comprising formic acid and a tertiary amine (I) in a molar ratio of from 0.5 to 5 by combining a tertiary amine (I) and a formic acid source;

(b) separating off from 10 to 100% by weight of the secondary components present in the liquid stream obtained from step (a) from said stream; and (c) removing formic acid by distillation in a distillation apparatus at a bottom temperature of from 100 to 300° C. and a pressure of from 30 to 3000 hPa abs from the liquid stream obtained from step (b);

wherein the tertiary amine (I) used is an amine which, at a pressure of 1013 hPa abs, has a boiling point at least 5° C. higher than formic acid, in addition the tertiary amine (I) to be used in step (a) and the separation rate in the distillation apparatus mentioned in step (c) are chosen so that two liquid phases form in the bottom discharge of the distillation apparatus mentioned in step (c) under the conditions prevailing in step (d), (d) separating the bottom discharge from the distillation apparatus mentioned in step (c) into two liquid phases, the upper liquid phase having a molar ratio of formic acid to tertiary amine (I) of from 0 to 0.5 and the lower liquid phase having a molar ratio of formic acid to tertiary amine (I) of from 0.5 to 5;

(e) recycling the upper liquid phase of the phase separation from step (d) to step (a); and (f) recycling the lower liquid phase of the phase separation from step (d) to step (b) and/or (c).

2. The process according to claim 1, wherein, in step (a), the stream comprising formic acid and a tertiary amine (I) is produced by hydrolysis of methyl formate in the presence of water and tertiary amine (I).

3. The process according to claim 1, wherein, in step (a), the stream comprising formic acid and a tertiary amine (I) is produced from dilute formic acid in the presence of tertiary amine (I).

4. The process according to claim 1, wherein the liquid stream produced in step (a) has a concentration of formic acid plus tertiary amine (I) of from 1 to 99% by weight, based on the total amount of the stream.

5. The process according to claim 1, wherein, in step (c), the stream comprising formic acid and a tertiary amine (I) is fed in the region of the lower fourth of the available separation stages.

6. The process according to claim 1, wherein, in step (c), the stream comprising formic acid and a tertiary amine (I) is fed to the bottom evaporator of the distillation apparatus.

7. The process according to claim 1, wherein the separation rate in the distillation apparatus mentioned in step (c) is chosen so that the molar ratio of formic acid to tertiary amine (I) in the bottom discharge is from 0.1 to 2.0.

8. The process according to claim 1, wherein metals and metal compounds present in the lower liquid phase formed according to step (d) are removed from said lower liquid phase.

9. The process according to claim 1, wherein the tertiary amine (I) used is an amine of the general formula (Ia)

$$NR^1R^2R^3 \quad \text{(Ia)},$$

in which the radicals $R^1$ to $R^3$ are identical or different and, independently of one another, are a straight-chain or branched, acyclic or cyclic, aliphatic, araliphatic or aromatic radical having in each case 1 to 16 carbon atoms, it being possible for individual carbon atoms, independently of one another, also to be substituted by a hetero-group selected from the group consisting of —O— and >N— and it being possible for two or all three radicals to be linked to one another with the formation of a chain comprising at least four atoms in each case.

10. The process according to claim 9, wherein the radicals $R^1$ to $R^3$, independently of one another, are selected from the group consisting of $C_1$- to $C_{12}$-alkyl, $C_5$- to $C_8$-cycloalkyl, benzyl and phenyl.

11. The process according to claim 10, wherein the radicals $R^1$ to $R^3$, independently of one another, are selected from the group consisting of $C_5$- to $C_8$-alkyl.

* * * * *